US007875280B2

(12) United States Patent
Schneewind et al.

(10) Patent No.: US 7,875,280 B2
(45) Date of Patent: Jan. 25, 2011

(54) METHODS AND COMPOSITIONS INVOLVING LCRV PROTEINS

(75) Inventors: Olaf Schneewind, Chicago, IL (US); Deborah M. Anderson, Naperville, IL (US); Robert Brubaker, Colombus, NC (US); Kristin L. DeBord, Washington, DC (US); R. William DePaolo, Chicago, IL (US); Katie A. Overheim, Chicago, IL (US); Elizabeth M. Morrin, Chicago, IL (US); Bana Jabri, Chicago, IL (US)

(73) Assignees: The University of Chicago, Chicago, IL (US); Michigan State University, East Lansing, MI (US)

( * ) Notice: Subject to any disclaimer, the term of this patent is extended or adjusted under 35 U.S.C. 154(b) by 598 days.

(21) Appl. No.: 11/293,024

(22) Filed: Dec. 2, 2005

(65) Prior Publication Data

US 2006/0177464 A1    Aug. 10, 2006

Related U.S. Application Data

(60) Provisional application No. 60/632,590, filed on Dec. 2, 2004.

(51) Int. Cl.
*A61K 39/02* (2006.01)
*C07H 21/00* (2006.01)
(52) U.S. Cl. .................................. 424/234.1; 536/23.7
(58) Field of Classification Search ....................... None
See application file for complete search history.

(56) References Cited

U.S. PATENT DOCUMENTS

| 5,985,285 | A | 11/1999 | Titball et al. | 424/234.1 |
| 6,638,510 | B1 | 10/2003 | Brubaker et al. | 424/184.1 |
| 6,964,770 | B2 | 11/2005 | Brubaker et al. | 424/234.1 |
| 2005/0232940 | A1 | 10/2005 | Brubaker et al. | 424/190.1 |

OTHER PUBLICATIONS

Sarker et al. (J. Bacteriol., 180:1207-1214, 1998.*
Harlow et al. (Antibodies, a Laboratory Manual, Cold Spring Harbor Laboratory, 1988, p. 67).*
Bello et al. (Plastic and Reconstructive Surgery, 119:1326-1336, 2007).*
Anderson et al., "Recombinant V antigen protects mice against pneumonic and bubonic plague caused by F1-capsule-positive and -negative strains of *Yersinia pestis*," *Infect. Immun.*, 64:4580-4585, 1996.
Anisimov et al, "Intraspecific diversity of *Yersinia pestis*," *Clin. Microbial. Rev.*, 17(2):434-464, 2004.
Bergman et al., "Analysis of the V antigen lerGVH-yopBD operon of *Yersinia pseudotuberculosis*: evidence for a regulatory role of LcrH and LcrV," *J. Bacteriol.*, 173:1607-1616, 1991.
Brubaker, "Interleukin-10 and inhibition of innate immunity to *Yersiniae*: roles of Yops and LcrV (V antigen)," *Infect. Immun.*, 71:3673-3681, 2003.
Brubaker, "Mutation rate to nonpigmentation in *Pasteurella pestis*," *J. Bacteriol.*, 98:1404-1406, 1969.
Derewenda et al, "The structure of *Yersinia pestis* V-antigen, an essential virulence factor and mediator of immunity against plague," *Structure*, 12:301-306, 2004.
Heath et al., "Protection against experimental bubonic and pneumonic plague by a recombinant capsular F1-V antigen fusion protein vaccine," *Vaccine*, 16:1131-1137, 1998.
Hill et al., "Regions of *Yersinia pestis* V antigen that contribute to protection against plague identified by passive and active immunization," *Infect. Immun.*, 65:4476-4482, 1997.
Jones et al., "Protection conferred by a fully recombinant sub-unit vaccine against *Yersinia pestis* in male and female mice of four inbred strains," *Vaccine*, 19(2-3):358-366, 2000.
Kopp and Medzhitov, "A plague on host defense," *J. Exp. Med.*, 196:1009-1012, 2002.
Leary et al., "Active immunization with recombinant V antigen from *Yersinia pestis* protects mice against plague," *Infect. Immun.*, 63:2854-2858, 1995.
Lee et al., "LcrV, a substrate for *Yersinia enterocolitica* type III secretion, is required for toxin targeting into the cytosol of HeLa cells," *J. Biol. Chem.*, 275:36869-36875, 2000.
Marketon et al., "Plague bacteria target immune cells during infection," *Science*,309:1739-1741, 2005.
Motin et al., "Passive immunity to yersiniae mediated by anti-recombinant V antigen and protein A-V antigen fusion peptide," *Infect. Immun.*, 62:4192-4201, 1994.
Motin et al., "V antigen-polyhistidine fusion peptide: binding to LcrH and active immunity against plague," *Infect. Immun.*, 64:4313-4318, 1996.
Nakajima and Brubaker, "Association between virulence of *Yersinia pestis* and suppression of gamma interferon and tumor necrosis factor alpha," *Infection and Immunity*, 61:23-31, 1993.
Nakajima et al., "Suppression of cytokines in mice by protein A-V antigen fusion peptide and restoration of synthesis by active immunization," *Infect. Immun.*, 63:3021-3029, 1993.
Nedialkov et al., "Resistance to lipopolysaccharide mediated by the *Yersinia pestis* V antigen-polyhistidine fusion peptide: amplification of interleukin-10," *Infection and Immunity*, 65:1196-1203, 1997.
Niles, "Dissecting the structure of LcrV from *Yersinia pestis*, a truly unique virulence protein," *Structure*, 12:357-358, 2004.
Overheim et al., "LcrV plague vaccine with altered immunomodulatory properties," *Infect. Immun.*, 73:5152-5159, 2005.

(Continued)

*Primary Examiner*—N M Minnifield
*Assistant Examiner*—Brian J Gangle
(74) *Attorney, Agent, or Firm*—Fulbright & Jaworski L.L.P.

(57) ABSTRACT

The present invention concerns methods and compositions involving modified LcrV proteins from *Yersinia* bacteria. These methods and compositions can be employed to invoke an immune response in a subject against the bacteria, while not suppressing the immune system as much as the native LcrV protein. In certain embodiments, the present invention relates to vaccines, as well as methods to protect a subject against *Yersinia pestis* and plague. Moreover, the present invention concerns methods and compositions for suppressing a subject's immune system using non-native LcrV polypeptides.

32 Claims, 12 Drawing Sheets

OTHER PUBLICATIONS

Perry and Fetherston, "*Yersinia pestis*—etiologic agent of plague," *Clin. Microbial. Rev.*, 10:35-66, 1997.

Pullen et al., "Analysis of the *Yersinia pestis* V protein for the presence of linear antibody epitopes," *Infect. Immun.*, 66:521-527, 1998.

Russell et al., "A comparison of Plague vaccine, USP and EV76 vaccine induced protection against *Yersinia pestis* in a murine model," *Vaccine*, 13:1551-1556, 1995.

Sawa et al., "Active and passive immunization with the Pseudomonas V antigen protects against type III intoxication and lung injury," *Nat. Med*., 5:392-398, 1999.
Sing et al., "Contribution of toll-like receptors 2 and 4 in an oral *Yersinia enterocolitica* mouse infection model," *Int. J. Med. Microbial*., 293:341-348, 2003.
Sing et al., "*Yersinia enterocolitica* evasion of the host innate immune response by V antigen-induced IL-10 production of macrophages is abrogated in IL-10-deficient mice," *J. Immunol*., 168:1315-1321, 2002.
Sing et al., "*Yersinia* V-antigen exploits toll-like receptor 2 and CD14 for interleukin 10-mediated immunosuppression," *J. Exp. Med*., 196:1017-1024, 2002.
Skrzypek and Straley, "Differential effects of deletions in lcrV on secretion of V antigen, regulation of the low-Ca2+ response, and virulence of *Yersinia pestis," J. Bacteriol*., 177:2530-2542, 1995.
Studier et al., "Use of T7 RNA polymerase to direct expression of cloned genes," *Methods Enzymol*., 185:60-89, 1990.
Titball and Williamson, "*Yersinia pestis* (plague) vaccines," *Expert Opin. Biol. Ther*., 4:965-973, 2004.
Une and Brubaker, "Roles of V antigen in promoting virulence and immunity in yersiniae," *J. Immunol*., 133:2226-2230, 1984.
Wang et al., "A DNA vaccine producing LcrV antigen in oligomers is effective in protecting mice from lethal mucosal challenge of plague," *Vaccine*, 22:3348-3357, 2004.
Welkos et al., "Determination of the virulence of the pigmentation-deficient and pigmentation-/plasminogen activator-deficient strains of *Yersinia pestis* in non-human primate and mouse models of pneumonic plague," *Vaccine*, 20:2206-2214, 2002.
Welkos et al., "Studies on the role of plasminogen activator in systemic infection by virulent *Yersinia pestis* strain C092," *Microb. Pathog*., 23(4):211-223, 1997.

* cited by examiner

```
         ---------+---------+---------+---------+---------+
              10        20        30        40        50
         ---------+---------+---------+---------+---------+
  1 MIRAYEQNPQHFIEDLEKVRVEQLTGHGSSVLEELVQLVKDKNIDISIKY  Y. pestis KIM LcrV
  1 MIRAYEQNPQHFIEDLENVRVEQLTGHGSSVLEELVQLVKDKNIDISIKY  Y. pestis Angola LcrV
  1 MIRAYEQNPQHFIEDLEKVRVEQLTGHGSSVLEELVQLVKDKNIDISIKY  Y. pestis CO92 LcrV
  1 MIRAYEQNPQHFIEDLEKVRVEQLTGHGSSVLEELVQLVKDKNIDISIKY  Y. pestis M26405 LcrV
  1 MIRAYEQNPQHFIEDLEKVRVEQLTGHGSSVLEELVQLVKDKNIDISIKY  Y. pestis str. 91001 LcrV
  1 MIRAYEQNPQHFIEDLEKVRVEQLTGHGSSVLEELVQLVKDKNIDISIKY  Y. pseudotb LcrV
  1 MIRAYEQNPQHFIEDLEKVRVEQLTGHGSSVLEELVQLVKDKRIDISIKY  Y. enterocolitica LcrV ---------+---------+---------+---------+---------+
              60        70        80        90       100
         ---------+---------+---------+---------+---------+
 51 DPRKDSEVFANRVITDDIELLKKILAYFLPEDAILKGGHYDNQLQNGIKR  Y. pestis KIM LcrV
 51 DPRKDSEVFANRVITDDIELLRKILAYFLPEDAILKGGHYDNQLQNGIKR  Y. pestis Angola LcrV
 51 DPRKDSEVFANRVITDDIELLKKILAYFLPEDAILKGGHYDNQLQNGIKR  Y. pestis CO92 LcrV
 51 DPRKDSEVFANRVITDDIELLKKILAYFLPEDAILKGGHYDNQLQNGIKR  Y. pestis M26405 LcrV
 51 DPRKDSEVFANRVITDDIELLKKILAYFLPEDAILKGGHYDNQLQNGIKR  Y. pestis str. 91001 LcrV
 51 DPRKDSEVFANRVITDDIELLKKILAYFLPEDAILKGGHYDNQLQNGIKR  Y. psuedotb LcrV
 51 DPKKDSEVFAERVITDDIELLKKILAYFLPEDAILKGGHYDNQLQNGIKR  Y. enterocolitica LcrV ---------+---------+---------+---------+---------+
             110       120       130       140       150
         ---------+---------+---------+---------+---------+
101 VKEFLESSPNTQWELRAFMAVMHFSLTADRIDDDILKVIVDSMNHHGDAR  Y. pestis KIM LcrV
101 VKEFLESSPNTQWELRAFMAVMHFSLTADRIDDDILKVIVDSMNHHGDAR  Y. pestis Angola LcrV
101 VKEFLESSPNTQWELRAFMAVMHFSLTADRIDDDILKVIVDSMNHHGDAR  Y. pestis CO92 LcrV
101 VKEFLESSPNTQWELRAFMAVMHFSLTADRIDDDILKVIVDSMNHHGDAR  Y. pestis M26405 LcrV
101 VKEFLESSPNTQWELRAFMAVMHFSLTADRIDDDILKVIVDSMNHHGDAR  Y. pestis str. 91001 LcrV
101 VKEFLESSPNTQWELRAFMAVIHFSLTADRIDDDILKVIVDSMNHHGDAR  Y. psuedotb LcrV
101 VKEFLESSPNTQWELRAFMAVMHFSLTADRIDDDILKVIVDSMNHHGDAR  Y. enterocolitica LcrV ---------+---------+---------+---------+---------+
             160       170       180       190       200
         ---------+---------+---------+---------+---------+
151 SKLREELAELTAELKIYSVIQAEINKHLSSSGTINIHDKSINLMDKNLYG  Y. pestis KIM LcrV
151 SKLREELAELTAELKIYSVIQAEINKHLSSSGTINIHDKSINLMDKNLYG  Y. pestis Angola LcrV
151 SKLREELAELTAELKIYSVIQAEINKHLSSSGTINIHDKSINLMDKNLYG  Y. pestis CO92 LcrV
151 SKLREELAELTAELKIYSVIQAEINKHLSSSGTINIHDKSINLMDKNLYG  Y. pestis M26405 LcrV
151 SKLREELAELTAELKIYSVIQAEINKHLSSSGTINIHDKSINLMDKNLYG  Y. pestis str. 91001 LcrV
151 SKLREELAELTAELKIYSVIQAEINKHLSSGGTINIHDKSINLMDKNLYG  Y. psuedotb LcrV
151 SKLREELAELTAELKIYSVIQAEINKHLSSSGTINIHEKSINLMDKNLYG  Y. enterocolitica LcrV ---------+---------+-------       --+---------+-
             210       220                  230       240
```

FIG. 1A

```
                ---------+---------+-------          --+---------+-
201 YTDEEIFKASAEYKILEKMPQTTIQVD███████GSEKKIVSIKDFLG  Y. pestis KIM LcrV
201 YTDEEIFKASAEYKILEKMPQTTIQVD███████GSEKKIVSIKDFLG  Y. pestis Angola LcrV
201 YTDEEIFKASAEYKILEKMPQTTIQVD███████GSEKKIVSIKDFLG  Y. pestis CO92 LcrV
201 YTDEEIFKASAEYKILEKMPQTTIQVD███████GSEKKIVSIKDFLG  Y. pestis M26405 LcrV
201 YTDEEIFKASAEYKILEKMPQTTIQVD███████GSEKKIVSIKDFLG  Y. pestis str. 91001 LcrV
201 YTDEEIFKASAEYKILEKMPQTTIQ██████████EKKIVSIK█FL█   Y. psuedotb LcrV
201 YTDEEIFKASAEYKIL█KMPQTTI█████████AG██IVSIK█FL█    Y. enterocolitica LcrV --------+---------+---------+---------+---------+-
                250       260       270       280       290
         --------+---------+---------+---------+---------+-
242 SENKRTGALGNLKNSYSYNKDNNELSHFATTCSDKSRPLNDLVSQKTTQL  Y. pestis KIM LcrV
242 SENKRTGALGNLKNSYSYNKDNNELSHFATT█SDKSRPLNDLVSQKTTQL  Y. pestis Angola LcrV
242 SENKRTGALGNLKNSYSYNKDNNELSHFATTCSDKSRPLNDLVSQKTTQL  Y. pestis CO92 LcrV
242 SENKRTGALGNLKNSYSYNKDNNELSHFATTCSDKSRPLNDLVSQKTTQL  Y. pestis M26405 LcrV
242 SENKRTGALGNLKNSYSYNKDNNELSHFATTCSDKSRPLNDLVSQKTTQL  Y. pestis str. 91001 LcrV
242 SE█KRTGALGNLK█SYSYNKDNNELSHFATTCSDKSRPLNDLVSQKTTQL  Y. psuedotb LcrV
251 SENKRTGALGNLK█SYSYNKDNNELSHFAT█CSDKSRPLNDLVSQKTTQL  Y. enterocolitica LcrV --------+---------+---------+------
                300       310       320
         --------+---------+---------+------
292 SDITSRFNSAIEALNRFIQKYDSVMQRLLDDTSGK     Y. pestis KIM LcrV
292 SDITSRFNSAIEALNRFIQKYDSVMQRLLDDTSGK     Y. pestis Angola LcrV
292 SDITSRFNSAIEALNRFIQKYDSVMQRLLDDTSGK.    Y. pestis CO92 LcrV
292 SDITSRFNSAIEALNRFIQKYDSVMQRLLDDTSGK     Y. pestis M26405 LcrV
292 SDITSRFNSAIEALNRFIQKYDSVMQRLLDDT█.      Y. pestis str. 91001 LcrV
292 SDITSRFNSAIEALNRFIQKYDSVMQRLLDDTSGK.    Y. psuedotb LcrV
301 SDITSRFNSAIEALNRFIQKYDSVMQRLLDDT█       Y. enterocolitica LcrV
```

FIG. 1B

```
Y. pestis KIM LcrV      .MIRAYEQNPQHFIEDLEKVRVEQLTGHGSSVLEELVQLVKDKNIDISIKYDPRKDSEVF
Y. enterocolitica LcrV  .MIRAYEQNPQHFIEDLEKVRVEQLTGHGSSVLEELVQLVKDKKIDISIKYDPKKDSEVF
Y. pseudotb LcrV        .MIRAYEQNPQHFIEDLEKVRVEQLTGHGSSVLEELVQLVKDKNIDISIKYDPRKDSEVF
P. aeruginosa PcrV      MEVRNLNAARELFLELLVASAARAEAELEELAALQSERIVTAEAGQPLSEAQVE Y. pestis KIM LcrV      ANRVITDDIELLKKILAYFLPEDAILKGGHYDNQLQNGIKRVKEFLES..SPNTQWELRA
Y. enterocolitica LcrV  AERVITDDIELLKKILAYFLPEDAILKGGHYDNQLQNGIKRVKEFLES..SPNTQWELRA
Y. pseudotb LcrV        ANRVITDDIELLKKILAYFLPEDAILKGGHYDNQLQNGIKRVKEFLES..SPNTQWELRA
P. aeruginosa PcrV      ANRVLTGKALAELLAVNPSAREGQSEAGEHVTLEVLSARRQPSAQWELRE Y. pestis KIM LcrV      FMAVMHFSLTADRIDDDILKVIVDSMNHHGDARSKLREELAELTAELKIYSVIQAEINKH
Y. enterocolitica LcrV  FMAVMHFSLTADRIDDDILKVIVDSMNHHGDARSKLREELAELTAELKIYSVIQAEINKH
Y. pseudotb LcrV        FMAVEHFSLTADRIDDDILKVIVDSMNHHGDARSKLREELAELTAELKIYSVIQAEINKH
P. aeruginosa PcrV      FEVSAYFSLEGERDEDEGVEKDVEGTQDGKRKALEEELKALTAELKEYSVIQSEINAE Y. pestis KIM LcrV      LSSSGTINIHDKSINLMDKNLYGYTD.EEIFKASAEYKILEKMPQTTIQVD.........
Y. enterocolitica LcrV  LSSSGTINIHEKSINLMDKNLYGYTD.EEIFKASAEYKILEKMPQTTIEDELLEVGVTA
Y. pseudotb LcrV        LSSEGTINIHDKSINLMDKNLYGYTD.EEIFKASAEYKILEKMPQTTIQEG........
P. aeruginosa PcrV      LSEKQEIEIDAGGIELEDEELYGYAVGEERLKESEEYAELSNEQELTSGE.........

Y. pestis KIM LcrV      GSEKKIVSIKDFLESENKRTGALGNLKNSYSYNKDNNELSHFATTCSDKSRPLNDLVSQK
Y. enterocolitica LcrV  GEEKEIVSIKEFLESENKRTGALGNLKESYSYNKDNNELSHFATECSDKSRPLNDLVSQK
Y. pseudotb LcrV        EEEKKIVSIKEFLESEEKRTGALGNLKESYSYNKDNNELSHFATTCSDKSRPLNDLVSQK
P. aeruginosa PcrV      EEEESIKDFLESESKQSGELKGLSEEYPEEKDNNEVGNFATTESDESRPLNDKVNEK Y. pestis KIM LcrV      TTQLSDITSRFNSAIEALNRFIQKYDSVMQRLLDDTSGK
Y. enterocolitica LcrV  TTQLSDITSRFNSAIEALNRFIQKYDSVMQRLLDDTEEE
Y. pseudotb LcrV        TTQLSDITSRFNSAIEALNRFIQKYDSVMQRLLDDTSGK
P. aeruginosa PcrV      TTELNDEESREENSAEEALNRFIQKYDSVERDELSAIEE
```

FIG. 2

```
rLcrV  [His] 1——————————————————326
rV1    [—] [31]
rV2    [—] 30  61
rV3    [—]    60  90
rV4    [—]      90  121
rV5    [—]        120  151
rV6    [—]           150  181
rV7    [—]              180  211
rV8    [—]                 210  241
rV9    [—]                    240  271
rV10   [—]                       270  301
rV11   [—]                          300
```

METHODS AND COMPOSITIONS INVOLVING LCRV PROTEINS

This application claims priority to U.S. Provisional Patent Application Ser. No. 60/632,590, filed on Dec. 2, 2004, which is hereby incorporated by reference.

The government may own rights in the present invention pursuant to grant number 1-U54-A1-057153 from the National Institutes of Health.

BACKGROUND OF THE INVENTION

1. Field of the Invention

The present invention relates generally to the fields of immunology and pathology. More particularly, it concerns methods and compositions involving the LcrV protein from *Yersinia* bacteria, particularly LcrV proteins that can be used to invoke an immune response against the bacteria while reducing the immunosuppressing effect of the native protein in a subject, as well as those that can be used because of their immunosuppressing effect. Therefore, the present invention includes preventative and therapeutic methods and compositions involving LcrV proteins.

2. Description of Related Art

*Yersinia pestis* is the causative agent of plague, a disease which likely killed more people worldwide than any other disease.

Early attempts at plague immunization employed avirulent live plague bacilli such as the non-pigmented EV76 strain (Meyer, 1970; Welkos et al., 2002). This approach was effective to prevent bubonic plague but too frequently resulted in complications such as inflammation, if not modest infection or even death (Bartelloni et al., 1973; Russell et al., 1995). Nevertheless, the process was utilized until recently in the Soviet Union even though numerous booster immunizations are required for full effectiveness. A similar, but less successful approach was the use of killed organisms in the United States (Williams and Cavanaugh, 1979). The general failure of these approaches has promoted considerable effort towards development of soluble subunit vaccines containing one or more protective antigens (Russell et al., 1995; Titball and Williamson, 2004). Vaccination with purified recombinant LcrV, a known protective antigen, elicits an immune response that protects experimental animals against plague (Une and Brubaker, 1984; Motin et al., 1994; Motin et al., 1996; Heath et al., 1998; Anderson et al., 1996; Leary et al., 1995). Other preparations of LcrV, whether alone or as a fusion to the Caf1 (F1) pilin subunit (Heath et al., 1998), extended these observations, revealing that antibodies against LcrV provide protection against bubonic and pneumonic plague.

Nakajima and Brubaker demonstrated that *Y. pestis* infection in mice is associated with the suppression of endogenous TNF-α and IFN-γ in vivo (Nakajima et al., 1995; Nakajima et al., 1993). Further, exogenous supply of TNF-α and IFN-γ, of rabbit polyclonal antisera against LcrV or of monoclonal antibody against LcrV could protect animals from a lethal infection with *Y. pestis* (Nakajima et al., 1995). Injection of purified recombinant LcrV preparations unequivocally demonstrated that LcrV functions as a protective antigen for plague and that antibodies against LcrV can be passively transferred to naive animals to achieve the same effect, which involves simultaneously the blockade of IL-10 secretion and restoration of endogenous TNF-α and IFN-γ release during animal infections with plague bacilli in vivo (Nakajima et al., 1995).

LcrV is absolutely required for human or animal infectious disease of three pathogenic *Yersinia* species, *Y. enterocolitica*, *Y. pseudotuberculosis*, and *Y. pestis* (Skrzypek and Straley, 1995; Bergmann et al., 1991; Lee et al., 2000). Heesemann and colleagues showed that Toll-like receptor 2 (TLR2) and CD14, but not TLR1 or TLR4, were required for *Yersinia* release of IL-10, and that deletion of the TLR2 gene resulted in resistance of mice to infections with pathogenic *Yersinia* spp. (Sing et al., 2002a; Sing et al., 2002b; Sing et al., 2003). Taken together, these observations not only document the central importance of LcrV in disease establishment, in modulating host immune functions and its use as a protective vaccine antigen, but also point to suppression of host immune responses as a serious obstacle for the vaccination of humans with purified recombinant LcrV.

To identify minimal components for plague vaccines, presumed linear epitopes of LcrV were divided into peptide segments of 30 amino acids or into truncated LcrV molecules lacking 100 or more amino acids (Pullen et al., 1998; Hill et al., 1997). Together these studies showed that immunization with small linear peptide epitopes (30 amino acids) provides no protection against plague, whereas large truncations of LcrV can elicit at least some protective immunity. However, previous studies did not take into consideration LcrV-mediated EL-10 release, and left unresolved whether plague vaccines without immune suppressive properties can be generated (Pullen et al., 1998; Hill et al., 1997). Therefore, there is a need for immunogenic compositions and methods that will elicit an immune response against pathogens such as *Yersinia pestis* but have less severe or negative immunosuppressing side effects.

SUMMARY OF THE INVENTION

The invention is based on studies showing that modified LcrV proteins, which are expressed by the *Yersinia* genus of bacteria, can induce an immune response in an animal yet stimulate the expression of immunosuppressing cytokines to a lesser extent or degree than an unmodified LcrV protein. Consequently, the invention generally relates to methods and compositions for inducing an immune response in a subject against *Yersinia* pathogens.

Compositions of the invention include recombinant polypeptides and cognate polynucleotides encoding such polypeptides. Polypeptides of the invention include a modified LcrV protein. The term "modified LcrV protein" will be understood as referring to a recombinant protein 1) whose sequence has been derived from a native LcrV protein (functional wild-type LcrV protein found to exist in a naturally occurring *Yersinia* bacteria), 2) but whose sequence has been altered through deletion, insertion, or substitution of one or more amino acids. It will further be understood that the "modified LcrV protein" is one that contains an amino acid sequence of any length recognizable as derived from a native LcrV protein from any *Yersinia* bacteria or as a consensus sequence for LcrV proteins from multiple *Yersinia* bacteria.

In some embodiments, the polypeptide contains a heterologous sequence with respect to the LcrV sequence. This heterologous sequence is in addition to the modified LcrV protein, and is an amino acid sequence that is recognizable as being from another peptide or polypeptide.

The modified LcrV proteins of the invention can be used to generate an immune response against *Yersinia* pathogens. It is particularly valuable because in some embodiments, polypeptides are immunogenic yet are less immunosuppressant than the corresponding unmodified *Yersinia* LcrV polypeptide. The term "immunogenic" is used according to its ordinary and plain meaning to indicate that a composition can provoke or induce an immune response. The term "immunosuppressant" is used according to its plain and ordinary meaning to refer to a composition that suppresses the immune system. It commonly refers to a drug or other compound that suppresses natural immune responses. The phrase "less immunosuppressant" refers to a composition that suppresses the immune system to a lesser or lower extent (a reduction of at least 50% or more in immunosuppressant activity) than a different composition, as measured by at least one assay indicative of immune system response. In most embodiments, a modified LcrV protein is less immunosuppressant compared to the "corresponding unmodified LcrV protein." In most embodiments, a modified LcrV protein is less immunosuppressant compared to the "corresponding unmodified *Yersinia* LcrV polypeptide," which refers to a polypeptide having the same *Yersinia* LcrV protein sequence from which the modified LcrV protein was derived, without any modifications. In certain embodiments, the present invention concerns a polypeptide comprising an immunogenic *Yersinia* LcrV protein that suppresses the immune system less than the full-length corresponding *Yersinia* LcrV polypeptide. The term "full-length" means a protein having a sequence and length that are the same as the native wild-type protein (protein found in nature). The term *Yersinia* LcrV protein will be understood to refer to an LcrV protein from a species within the *Yersinia* genus. In certain embodiments, the species is a pathogenic member of *Yersinia*.

The extent of immunosuppression can be evaluated directly or indirectly. In some embodiments, immunosuppression is determined indirectly, such as by evaluating induction of immunomodulatory cytokines that mediate immunosuppression. Interleukin 6 (IL-6) and IL-10 are examples of such cytokines. Therefore, in some embodiments of the invention, modified LcrV proteins induce expression of IL-6 or IL-10, or both cytokines, less than the full-length corresponding *Yersinia* LcrV polypeptide. In other words, the full-length LcrV protein leads to greater amounts of IL-6 and/or IL-10 protein being expressed in that organism or a comparable organism exposed to the modified version of that full-length LcrV protein. This can be evaluated by methodlogy known to those of skill in the art, such as is described in the Examples.

It is contemplated that in some aspects of the invention, the decrease in immunosuppression is about 2-, 3-, 4-, 5-, 6-, 7-, 8-, 9-. 10-, 11-, 12-, 13-, 14-, 15-, 20- , 25-, 30-, 35-, 40-, 45-, 50-, 55-, 60-, 65-, 70-, 75-, 80-, 85-,90-, 100-, 125-, 150-, 200-, 250-, 300-, 400-, 500-, 600-, 700-, 800-, 900-, 1000-fold, or any range derivable therein, relative to the corresponding full-length or unmodified LcrV polypeptide, as measured by a specific assay. Alternatively, this may be expressed in terms of percentage of unmodified activity, such as about, at least about, or at most about 1, 5, 10, 15, 20, 25, 30, 35, 40, 45, 50, 55, 60, 65, 70, 75, 80, 85% or any range derivable therein with respect to the activity of the corresponding unmodified LcrV polypeptide by a specific assay. Therefore, it is clearly contemplated that in some embodiments a modified LcrV protein does not qualify as being "less immunosuppressant" (50% reduction or greater) than the full-length, unmodified protein, but has only 60% of the immunosuppressant activity of the full-length, unmodified protein. Any embodiment discussing a modified LcrV polypeptide that is "less immunosuppressant" than an unmodified polypeptide may be implemented with a modified LcrV polypeptide that has a reduced ability to suppress the immune system, but that is not reduced to at least 50%. In certain embodiments, a modified LcrV polypeptide does not "significantly suppress" the immune system, which means it suppresses the immune system 50% or less than the extent of the corresponding full-length or unmodified corresponding LcrV polypeptide in at least one assay for immunosuppression.

In certain embodiments a modified LcrV protein suppresses the expression of a pro-inflammatory cytokine to a lesser extent than a corresponding unmodified LcrV protein. Pro-inflammatory cytokines are well known. In some embodiments, the pro-inflammatory cytokine is TNF-α. It is contemplated that in some aspects of the invention, the decrease in suppression of TNF-A expression is about 2-, 3-, 4-, 5-, 6-, 7-, 8-, 9-, 10-, 11-, 12-, 13-, 14-, 15-, 20-, 25-, 30-, 35-, 40-, 45-, 50-, 55-, 60-, 65-, 70-, 75-, 80-, 85-, 90-, 100-, 125-, 150-, 200-, 250-, 300-, 400-, 500-, 600-, 700-, 800-, 900-, 100-fold, or any range derivable therein, relative to the corresponding full-length or unmodified LcrV polypeptide, as measured by a specific assay. Alternatively, this may be expressed in terms of percentage of unmodified activity, such as about, at least about, or at most about 1, 5, 10, 15, 20, 25, 30, 35, 40, 45, 50, 55, 60, 65, 70, 75, 80, 85% or any range derivable therein with respect to the activity of the corresponding unmodified LcrV polypeptide by a specific assay.

A variety of modifications in an LcrV protein are contemplated. In some embodiments, the modification is in the LcrV protein from *Yersinia pestis*. These modified LcrV proteins are immunogenic in some embodiments of the invention. In other embodiments, the modified LcrV proteins suppress the immune system to a lesser extent than the full-length corresponding LcrV protein. In some embodiments, the modified LcrV protein is immunogenic (may be less, more or as immunogenic as the corresponding full-length LcrV protein) and less immunosuppressant than the corresponding full-length LcrV protein.

These immunogenic proteins can be polypeptides (100 amino acids or longer) or peptides (less than 100 amino acids in length). In certain embodiments, modified LcrV proteins that are less immunosuppressant than the corresponding full-length LcrV protein are not peptides. Moreover, it is contemplated that in some embodiments of the invention, a modified LcrV protein that is less immunosuppressant than the corresponding full-length or unmodified LcrV protein (also referred to as cognate LcrV protein) suppresses the immune system by less than 50, 45, 40, 35, 30, 25, 20, 15, 10, 5, 1% or less (or any range derivable therein) compared to the corresponding full-length or unmodified LcrV protein according to at least one assay. For example, a modified LcrV protein may have less than 10% of the immunosuppressant activity of the cognate LcrV protein.

In some embodiments, the modification is a deletion relative to the full-length corresponding *Yersinia* LcrV protein. The deletion is of, of at least, or of at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, or 321 contiguous residues of a full-length LcrV protein, or any range derivable therein. In certain embodiments, the deletion is up to 321, up to 250, up to 200, up to 163, up to 150, up to 100, up to 60, up to 45, up to 35, up to 31 or up to 26 contiguous residues, but is understood to have at least 1 residue deleted. In most embodiments, a modified LcrV protein with a deletion has at least 3 contiguous amino acids deleted.

Moreover, it will be understood that multiple deletions of contiguous amino acids are contemplated. Additionally, a deletion may be an internal deletion, meaning the deletion does not encompass the residue at the amino end or the carboxy end of the full-length LcrV protein. In addition to any deletion discussed above, an internal deletion is up to 90, 60, or 31 contiguous residues in some embodiments of the invention. In other embodiments, an internal deletion extends into the region spanning amino acids 240 to 325 or the region spanning amino acids 260 to 325 relative to the full-length LcrV protein from *Yersinia pestis*, meaning that the deletion includes one or more amino acids upstream and/or downstream of the specified region and at least one amino acid in the specified region. In particular embodiments, the deletion may be of the entire region. In some embodiment, the deletion includes the region 271 to 300, while in other embodiments, the deletion consists of the region from amino acid 271 to amino acid 300 (rV10). It is contemplated that the same amino acids corresponding to that region of LcrV from *Yersinia pestis* may be deleted in other LcrV proteins after the necessary adjustment is made in the amino acid numbering. For example, amino acids 271-300 in *Yersinia pestis* corresponds to 280-309 in *Y. enterocolitica*, as shown in FIG. 1. The skilled artisan would know how to align LcrV proteins from different species and determine a region that corresponds to a specified modified region.

In certain embodiments, the internal deletion may be such that there is, is at least, or is at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, or 324 contiguous amino acids present from the amino and/or carboxy of the full-length LcrV protein (the numbers of amino acids at the amino and carboxy ends will, of course, equal the appropriate number of total amino acids, depending on the length(s) of the deletions), or any range derivable therein.

Alternatively, in some cases the deletion is not an internal deletion. In some embodiments, the deletion is a C-terminal deletion of up to 50 contiguous residues. It is contemplated that polypeptides of the invention having a C-terminal deletion are missing, are missing at least, or are missing at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or more contiguous amino acids at their C-terminal end compared to a full-length polypeptide, or any range derivable therein.

Polypeptides of the invention contain a modified LcrV polypeptide that is contemplated to be shorter in length than their full-length counterpart in some embodiments of the invention. It is contemplated that truncated LcrV polypeptides of the invention may be, be at least, or be at most 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, or 333 amino acids in length, or any range derivable therein. LcrV full-length polypeptides from *Y. pestis* strains are 325 or 326 amino acids in length, while an LcrV polypeptide from *Y. enterocolitica* is 333 amino acids in length. However, it is also contemplated that polypeptides of the invention may have a truncated LcrV protein but are longer because they are a fusion or chimeric protein, such as by having a protein tag attached. It is further contemplated that a modified LcrV protein may have more than one non-contiguous region (a region is two or more amino acids) deleted compared to a full-length sequence. The deletions may be internal deletions, terminal deletions, and/or a combination thereof.

It is contemplated that any embodiment concerning a modified LcrV protein with a deletion applies to a modified LcrV protein in which instead of a deletion concerning particular amino acids, those amino acids are substituted with non-homologous amino acids. Therefore, in some embodiments of the invention, there are modified LcrV proteins in which, in which at least or in which at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, or 333 contiguous or noncontiguous amino acids have been replaced with a non-homologous amino acid, or any range in between. A non-homologous amino acid refers to a replacement with an amino acid that is not a "like amino acid" as discussed herein.

The present invention further concerns compositions comprising an immunogenic *Yersinia* LcrV protein that suppresses the immune system less than the full-length corresponding *Yersinia* LcrV polypeptide, wherein the composition is in a pharmacologically acceptable formulation. It is contemplated that such compositions can be used to generate an immune response in a subject having an immune system. It is particularly desirable that these compositions can generate a protective immune response against a *Yersinia* member pathogen, such as *Yersinia pestis*. A "protective immune response" refers to an immune response that can protect the subject from a disease caused by a pathogenic organism, such as *Yersinia pestis*. In the case of *Yersinia pestis*, the subject can have immunity or relative immunity against the plague or other diseases caused by infection with a *Yersinia* pathogen. In some embodiments of the invention, a composition further comprises one or more adjuvants. In certain cases, the adjuvant is conjugated or fused to the polypeptide or nucleic acid encoding the polypeptide. The composition may also include a carrier, in certain embodiments of the invention.

Polynucleotides are also included as part of the present invention. Such polynucleotides are recombinant and they encode LcrV proteins that can induce an immune response against the protein. An immune response against the protein generates, in some embodiments, a protective immune response against the pathogen from which it was derived. Polynucleotides of the invention include any DNA or RNA sequence encoding a modified LcrV polypeptide discussed above. In certain embodiments, a DNA vaccine encoding a modified LcrV protein is provided, particularly one that is immunogenic but that suppresses the immune system less than the corresponding full-length LcrV polypeptide.

The current invention can be used as a sole antigen for plague vaccination or in combination with other *Yersinia* antigens that also contribute to generating a protective immune response in either experimental animals or humans for diagnostic and therapeutic purposes. Examples include, but are not limited to, the F1 (Caf1, capsular antigen fraction 1) of *Yersinia pestis* which is known as a purified antigen to elicit a protective immune response in some experimental systems.

In some embodiments of the invention, a polynucleotide is a vector comprising a nucleic acid sequence encoding a modified LcrV polypeptide. It is contemplated that such a vector can include a promoter operably linked to the modified LcrV-encoding sequence, particularly a promoter that provides expression in the cells of a subject in which an immune response is desired. Therefore, it is contemplated that in some embodiments of the invention, the promoter can direct transcription in a mammalian cell.

It is specifically contemplated that polypeptides and polynucleotides of the invention may be comprised in a pharmacologically acceptable formulation. Furthermore, in some embodiments of the invention a polypeptide or polynucleotide is formulated with an adjuvant. In some embodiments of the invention the adjuvant is conjugated or fused to the polypeptide or polynucleotide. Thus, in some embodiments of the invention, compositions constitute a vaccine against a disease or conditions related to one or more *Yersinia* pathogen.

The LcrV protein can be derived from any *Yersinia* bacteria against which an immune response is desired. The sequences of these different LcrV proteins are known.

In certain embodiments of the invention, a response against a pathogen from the *Yersinia* genus is desired. In some cases, the *Yersinia* pathogen is *Yersinia pestis, Yersinia enterocolitica*, or *Yersinia pseudotuberculosis*.

The present invention also concerns methods of stimulating an immune response against a *Yersinia* pathogen in a subject comprising administering to the subject an effective amount of a composition comprising an immunogenic *Yersinia* LcrV protein that suppresses the immune system less than the full-length corresponding *Yersinia* LcrV polypeptide, wherein the composition is in a pharmacologically acceptable formulation.

In particular embodiments, the *Yersinia* LcrV protein is a modified protein. As discussed above, the protein contains a deletion relative to the full-length *Yersinia* LcrV protein according to some embodiments of the invention. In certain embodiments, the modified protein is rV10 or derived from rV10 (a modified protein deleted for at least amino acids 271-300 and containing further modifications—deletions, insertions, or substitutions—relative to rV10). It is particularly contemplated that the subject is one in which *Yersinia* species are pathogenic. The subject is specifically contemplated to be a mammal, including, but not limited to, a human, monkey, rat, mouse, rabbit, gorilla, pig, horse, prairie dog, gerbil, dog, cat or cow, or any carrier or host for a *Yersinia* pathogen.

Aspects of the invention include methods of stimulating an immune response against a *Yersinia* pathogen in a subject comprising administering to the subject an effective amount of a composition that includes an immunogenic LcrV polypeptide comprising an internal deletion extending in the region spanning amino acids 240 to 325, wherein the composition is in a pharmacologically acceptable formulation. In certain embodiments, the composition includes a polypeptide that is rV10 or derived from rV10.

Methods of the invention also include methods for stimulating an immune response against a *Yersinia* pathogen in a subject comprising administering to the subject an effective amount of a composition that includes an immunogenic LcrV polypeptide comprising a C-terminal deletion of up to 50 contiguous residues, wherein the composition is in a pharmacologically acceptable formulation. In certain embodiments, the composition includes a polypeptide that is rV10 or derived from rV10.

Other aspects of the invention include a method of stimulating a protective immune response against a *Yersinia* pathogen in a mammal comprising administering to the mammal an effective amount of a vaccine comprising a modified immunogenic *Yersinia* LcrV protein that is not an immunosuppressant relative to a full-length LcrV polypeptide, wherein the vaccine is in a pharmacologically acceptable formulation and when administered to a mouse stimulates a protective immune response against *Yersinia*. In certain embodiments, the modified immunogenic *Yersinia* LcrV protein is rV10 or derived from rV10.

It is contemplated that the different methods of stimulating an immune response may be implemented prior to infection by the *Yersinia* pathogen or after infection by the pathogen. In the latter embodiments, the modified LcrV proteins, such as rV10 or a derivative thereof, are used for their neutralizing activity in a post-exposure therapy. Thus, in these embodiments, methods may further include identifying or diagnosing a patient infected with a *Yersinia* pathogen or at risk for a prior exposure or identifying a patient in need of the treatment. Furthermore, embodiments may involve treating the patient with an effective amount of a modified LcrV protein, wherein an effective amount is an amount that provide a therapeutic benefit with respect to the infection, such as a decrease in the number of bacteria, alleviation or reduction in one or more symptoms, reducing the risk of fatality, reducing the length of time of infection, and improving chances of recovery. In additional embodiments, the patient is given the LcrV modified protein as a post-exposure therapy in conjunction with traditional antibacterial treatment such as treatment with an antibiotic.

Other methods provide a method of immunizing a subject against plague comprising administering to the subject an effective amount of an immunogenic, modified LcrV polypeptide that suppresses the immune system less than a corresponding unmodified LcrV polypeptide, whereby the subject develops an immune response against the polypeptide. In certain embodiments, the immunogenic, modified LcrV polypeptide is rV10 or derived from rV10. Furthermore, it is contemplated that the type of plague may be bubonic and/or pneumonic plague.

The invention may also be described in terms of an ability to convey protection against a *Yersinia* pathogen. In some embodiments of the invention, there are methods of protecting a subject from developing a disease comprising administering to the subject an effective amount of a modified LcrV polypeptide, wherein the modified LcrV polypeptide is more protective than the corresponding unmodified LcrV polypeptide. This may be tested, for example, using an intranasal challenge in an animal disease model. The test may involve a challenge of about, at least about, or at most about 500, 1,000, 10,000, 25,000, 50,000, 75,000, 100,000, 125,000, 150,000, 175,000, 200,000 $LD_{50}$ or mean lethal doses (MLD) or more, or any range derivable therein. In certain embodiments, the modified LcrV polypeptide may be more immunogenic and/or suppresses the immune system to a lesser extent than the corresponding unmodified LcrV polypeptide. Furthermore, the modified LcrV polypeptide may be rV10 or derived from rV10.

It is contemplated that any immunogenic LcrV polypeptide or encoding nucleic acid discussed herein may be implemented or employed in methods of the invention. It is also contemplated that any protective or vaccination method of the invention may apply in the context of protection or vaccination against a fully virulent *Yersinia* pathogen or isolate.

In some methods of the invention, a composition is administered multiple times. It is contemplated that the subject has an immune response against the modified LcrV protein in some embodiments of the invention, which may be a protective immune response. Moreover, a composition may be administered at least or at most 2, 3, 4, 5, 6 or more times to a subject. Subsequent administrations are considered a booster shot in some embodiments of the invention. Additionally, a composition may be administered to a subject on a regular basis, such as once a year or once every 2, 3, 4, 5, 6, 7, 8, 9, 10 or more years in order to maintain protective immunity. Moreover, it is contemplated that when a composition is given more than one time, other administrations could be of the same amount, dosage, or concentration as the initial composition or other administrations, or any of these parameters may be different with respect to the initial administration or any subsequent administration.

Methods of the invention include where the composition is administered to the subject intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intrathecally, subcutaneously, subconjunctival, intravesicularlly, mucosally, intrapericardially, intraumbilically, intraocularly, orally, locally, by inhalation, by injection, by infusion, by continuous infusion, by localized perfusion, via a catheter, via a lavage, in a creme, or in a lipid composition.

In certain embodiments, a composition stimulates a protective immune response. In still further embodiments, a composition does not significantly suppress the immune system of the subject.

Methods of the invention also relate to screening for a modified LcrV protein that stimulates an immune response and whose immunostimulatory properties are modulated with respect to the corresponding unmodified full-length LcrV protein. Such methods involve assaying a modified LcrV protein for immunogenicity and immunostimulatory properties. Immunogenicity may be evaluated by measuring indicators of immunogenicity, such as a T-cell and/or B cell response, and/or by assaying protective immunity conferred by the modified LcrV protein. Furthermore, such methods may involve evaluating the ability of the modified LcrV protein to stimulate the immune system, which may also involve measuring indicators of immunostimulation. For instance, downregulation of one or more compounds known to stimulate the immune system (for example, a cytokine) may be measured and/or upregulation of one or more compounds that suppress the immune system (for example, a different cytokine) may be measured. Such methods may involve testing of the compound, such as in an appropriate animal model. Further testing may involve human subjects for safety and efficacy.

The present invention also concerns compositions and methods relating to a modified LcrV protein that suppresses the immune system almost as well, if not as good as, a native or unmodified LcrV polypeptide. Such "immunosuppressant *Yersinia* LcrV proteins" have an immunosuppressant activity that is 80% or more of the activity of a native or unmodified LcrV polypeptide. Thus, in some embodiments of the invention there are compositions comprising an immunosuppressant *Yersinia* LcrV protein that is isolated and modified. It is contemplated that the LcrV protein is modified by having a deletion, insertion, or substitution of one or more amino acids. Such proteins include those found in FIG. 3, such as rV8 and rV9. These immunosuppressant proteins can be polypeptides (100 amino acids or longer) or peptides (less than 100 amino acids in length).

The invention includes, in some embodiments, methods of suppressing the immune system in a patient comprising: a) identifying a patient in need of such treatment; and, b) administering to the patient an effective amount of a composition comprising a *Yersinia* LcrV protein. Other aspects include a method of suppressing the immune system in a patient comprising administering to the patient an effective amount of a composition comprising an immunosuppressant *Yersinia* LcrV protein, wherein the protein has a deletion, and wherein the composition is in a pharmaceutically acceptable formulation. An effective amount with respect to suppressing the immune system means that the level of immune suppression is 80% or more the level of immune suppression induced by a full-length unmodified or native LcrV protein.

A patient may be determined to be in need of the treatment after taking a patient history or running a test. In certain embodiments, the patient has been diagnosed with, has symptoms of, or is at risk for an autoimmune disease, graft versus host disease or organ transplant rejection.

Any embodiment discussed with respect to methods of stimulating an immune response using an immunogenic but less immunosuppressant modified LcrV protein may be implemented with respect to immunosuppressing methods of the invention. Moreover, it is contemplated that any embodiment discussed with respect to methods of stimulating an immune response using an immunogenic but less immunosuppressant modified LcrV protein may be implemented with different modified LcrV proteins discussed herein, including the Examples.

Generally, it is contemplated that any method or composition described herein can be implemented with respect to any other method or composition described herein.

Throughout this application, the term "about" is used to indicate that a value includes the standard deviation of error for the device or method being employed to determine the value.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

It is specifically contemplated that any embodiments described in the Examples section are included as an embodiment of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-B. Amino acid sequence alignment of LcrV from different *Y. pestis* strains. The shaded region shows sequence differences (pestis KIM LcrV (SEQ ID NO:1); pestis Angola LcrV (SEQ ID NO:2); pestis CO92 LcrV and pestis M26405LcrV (SEQ ID NO:3); pestis str. 91001 LcrV (SEQ ID NO:4); psuedotb LcrV (SEQ ID NO:5); enterocolitica LcrV (SEQ ID NO:6)).

FIG. 2. Amino acid sequence alignment of LcrV from *Y. pestis* (SEQ ID NO:1), *Y pseudotuberculosis* (SEQ ID NO:5) and *Y. enterocolitica* (SEQ ID NO:6) with *Pseudomonas aeruginosa* PcrV (SEQ ID NO:44). Residues that are identical to *Y. pestis* LcrV were not shaded, whereas dark shading marks similar and light shading indicates dissimilar amino acids. Residues 31-49, encompassing the LcrV peptide of *Y. enterocolitica* that is sufficient to activate IL-10secretion, have been underlined (Sing et al., 2002a).

FIG. 3. Recombinant LcrV and its variants. Full length wild-type *Y. pestis*strain KIM lcrV was expressed as an N-terminal decahistidyl fusion protein from T7 polymerase expression vector pET16b. Recombinant lcrV variant genes encoding staggered 30 amino acid deletions were generated from PCR amplified DNA fragments and expressed under the same conditions. rLcrV or rV1-11 were purified by affinity chromatography on Ni-NTA and eluted with imidazole. After TRITON-X114 detergent extraction of endotoxin, proteins were purified on Sephadex G25.

FIG. 7. rV10 protects mice against lethal plague challenge. (A) Mice were immunized on day 0 and 21 by intra-muscular injection with 100 μg of purified protein (rLcrV, rV9, rV10 or rV11) emulsified with ALHYDROGEL™ or with adjuvant alone. On day 43 after the first immunization, animals were challenged by intra-venous infection with 1,000 $LD_{50}$ doses of *Y. pestis* KIM D27 and survival was measured. (B) Mean serum IgG titers in blood on day 42 after immunization with rLcrV and its variant proteins. Groups of BALB/c mice were immunized with rLcrV proteins on day 0 and 21. Mice were bled on day 0, 14, 28 and 42. Serum samples were analyzed for rLcrV specific IgG by custom ELISA.

Figure 9:
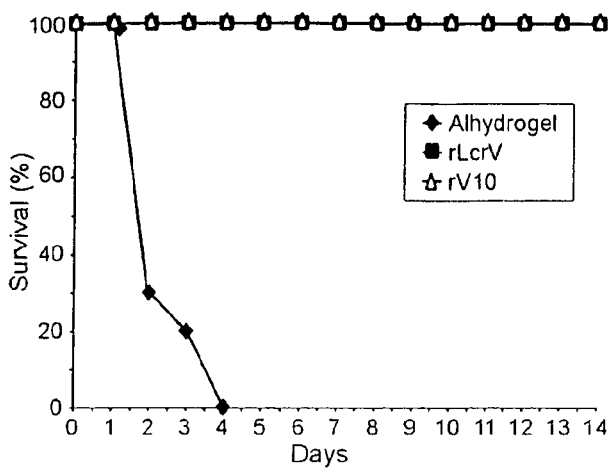

FIG. 9. Vaccination of mice with rV10 provides protection against bubonic plague. BALB/c mice were immunized intramuscularly with adjuvant alone (ALHYDROGEL)™, rLcrV or rV10 in a two dose regimen (50 μg antigen injected on day 0 and21). On day 43 post-immunization, mice were challenged with 100,000 MLD of *Y. pestis* CO92by subcutaneous injection. Animals were monitored over 14 days.

Figure 10:
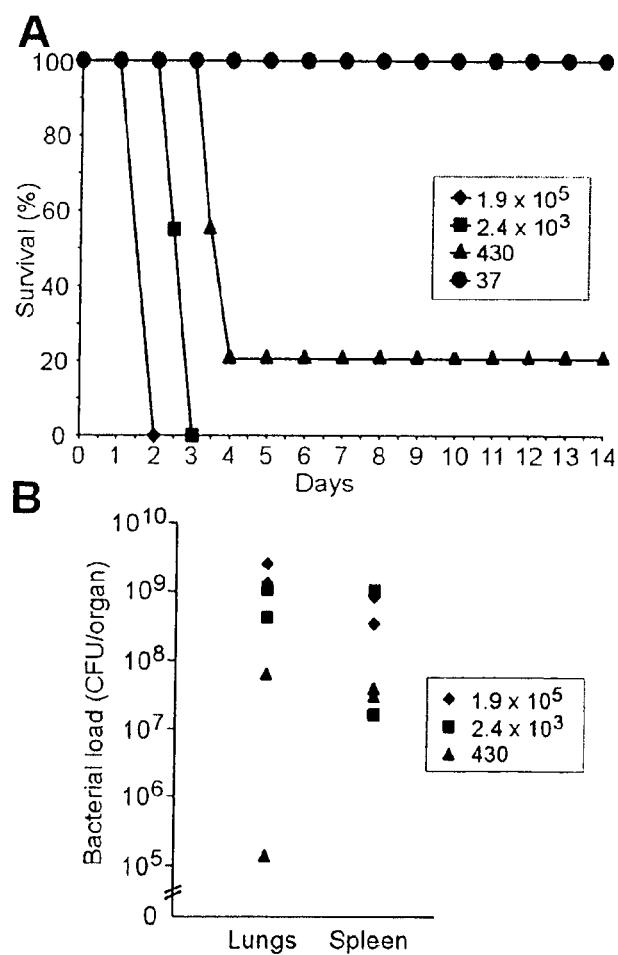

FIG. 10A-B. Inoculation of *Y. pestis* CO92 into the nares of anesthetized mice precipitates rapidly lethal pneumonic plague disease and systemic infection. (A) BALB/c mice were inoculated with varying doses of *Y. pestis* CO92 as shown in the inset via intranasal instillation. Animals succumbed to infection within 4 days of infection. (B) Animals showing signs of terminal illness were humanely culled by $CO_2$ asphyxiation and their lungs and spleens harvested for enumeration of bacteria. Both lungs and spleens harbored large numbers of *Y. pestis* CO92 suggesting rapid dissemination of disease.

Figure 11:
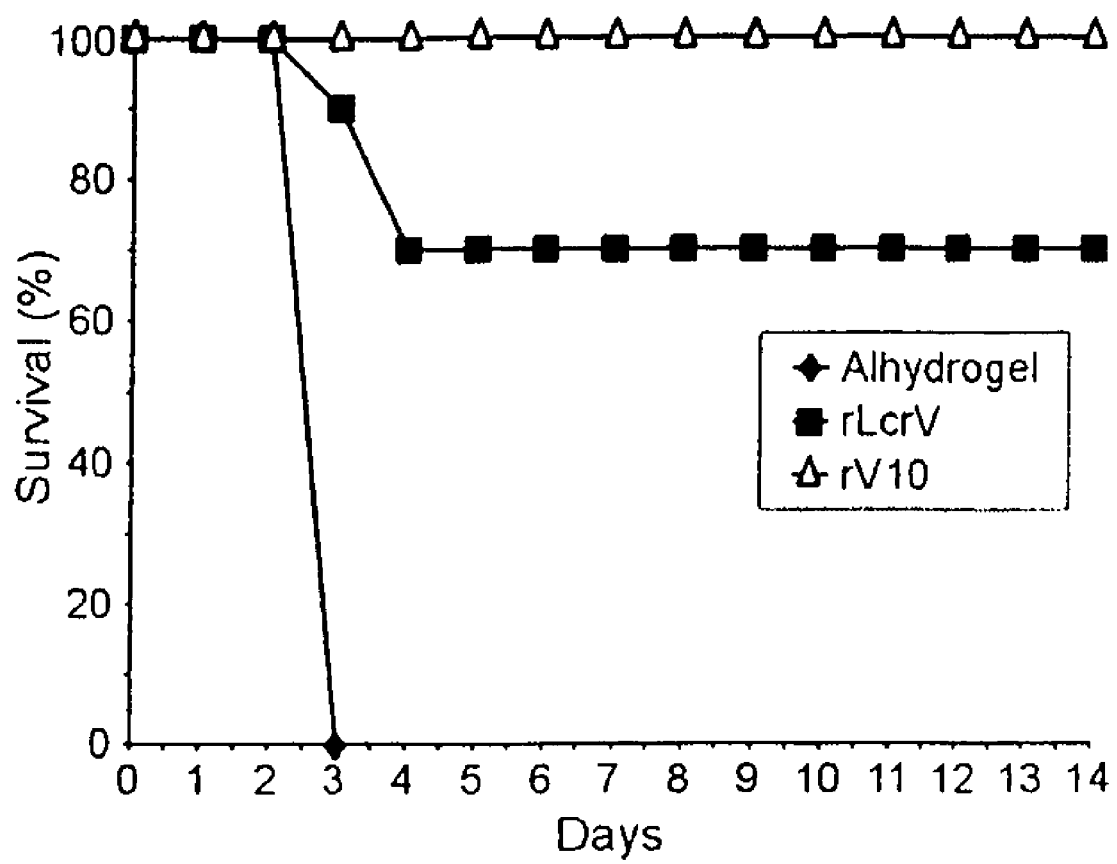

FIG. 11. Vaccination of mice with rV 10 provides protection against pneumonic plague. BALB/c mice were immunized intramuscularly following the standard two dose regimen with adjuvant alone, rLcrV or rV10. On day 43 post-immunization, mice were challenged with 1,000,000 CFU (equivalent to 2,570 MLD) *Y. pestis* CO92 via intranasal instillation. Mice were monitored for 14 days. All adjuvant mice succumbed to disease within 3 days, whereas rV10 vaccinated mice were completely protected.

Figure 12A:
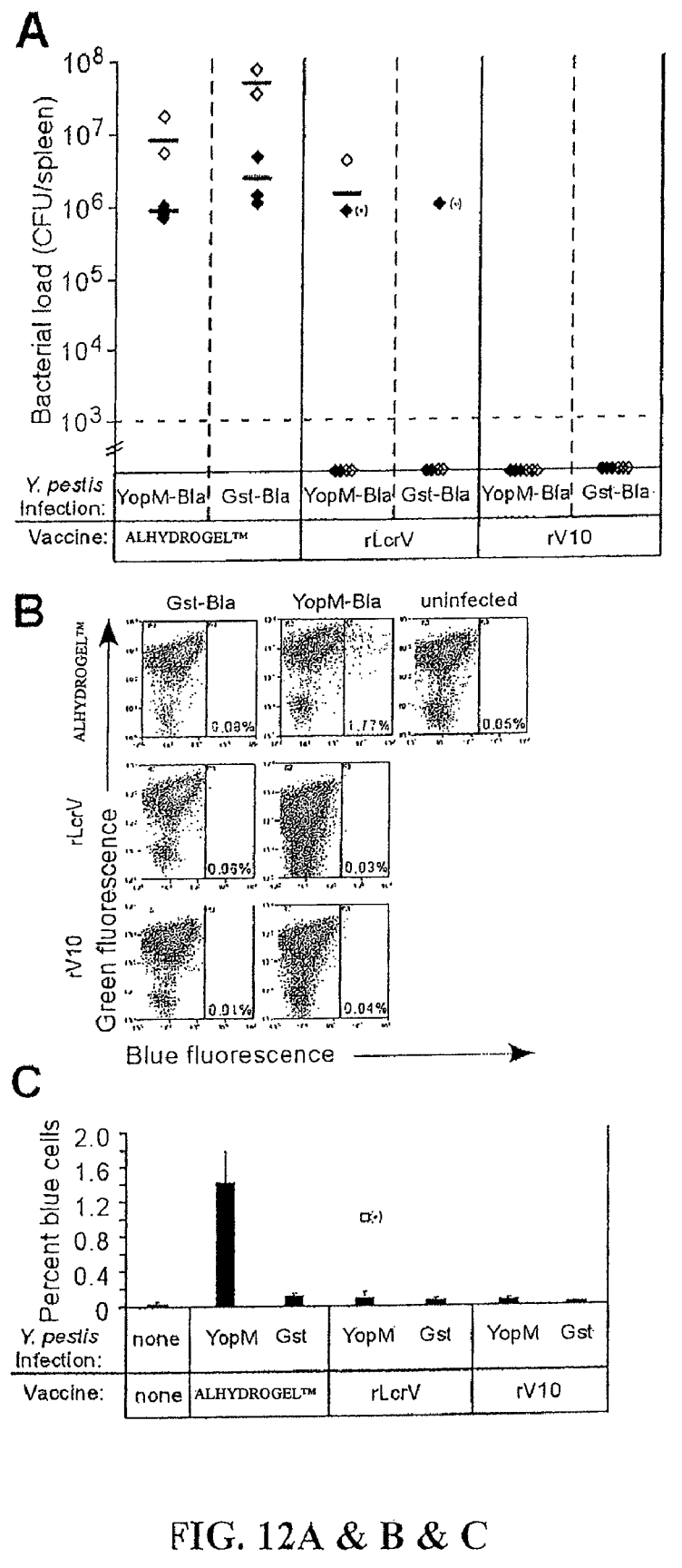

FIG. 12A-C. Effect of rLcrV and rV10 immunization on plague pathogenesis. (A) *Y pestis* strain KIMD27 carrying plasmids pMM83 (for expression and type III injection of YopM-Bla) or pMM91 (for expression-but not type III secretion-of Gst-Bla) were used for intravenous infection of mice that had been immunized with adjuvant alone (ALHYDROGEL)™, rLcrV or rV10. Bacterial load in the spleen of infected animals was quantified by colony formation of tissue homogenate. Dashed line indicates the limit of detection. (B) *Yersinia* type III injection of splenic phagocytes measured with CCF2-AM staining (blue fluorescence) and flow cytometry of cells isolated from representative animals (A) immunized with ALHYDROGEL™ (control), rLcrV or rV10. (C) Summary of *Yersinia* type III injection measurements in multiple infected animals.

Figure 13:
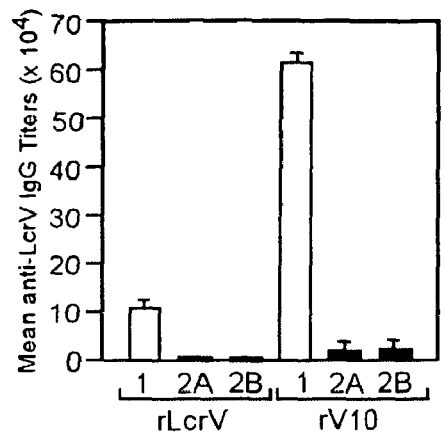

FIG. 13. Sera from 5 mice in each vaccination group were analyzed for IgG titer by ELISA. rV10 vaccination resulted in higher titers of IgG1, 2a and 2b as compared to animals vaccinated with rLcrV.

FIG. 14A-B. Murine T-cells are responsive to immunization with rV10 or rLcrV. BALB/c mice were immunized with 100 μg LcrV, rV10 or the non-immunomodulatory *Pseudomonas aeruginosa* rPcrV antigen. Eight days post-immunization, lymph nodes were harvested and T-cells purified by magnetic beads. These T-cells were then stimulated with homologous antigen (A) or with rLcrV (B).

DESCRIPTION OF ILLUSTRATIVE EMBODIMENTS

I. *Yersinia*

A. *Yersinia pestis* and Plague

Plague epidemics have likely killed more people worldwide than any other infectious disease (Perry and Fetherston, 1997; Ziegler, 1991). Mammals, in particular rats, prairie dogs and gerbils, are the primary reservoir of *Y. pestis* and human disease transmission occurs by flea bite, aerosol or contact (Craven et al., 1993; Davis et al., 2004). Flea bite *Y. pestis* infection leads to bubonic plague with characteristic lymph node swellings and disease symptoms that progress frequently to systemic infection and pneumonia (Butler, 1983; Boisier et al., 2002). Aerosol transmission of virulent *Y. pestis*, whether during plague epidemics or deliberate dissemination, precipitates pneumonic plague, a rapidly fatal disease with few characteristic symptoms (Meyer, 1961). Considering the ubiquitous zoonotic nature of the disease and the possible illegitimate use of *Y. pestis* as a weapon, there is an urgent need for vaccine development to protect humans against bubonic and pneumonic plague (Perry and Fetherston, 1997).

The incubation period of bubonic plague is 1-6 days (Butler, 1983). Clinical symptoms appear abruptly with high fever, malaise, tachycardia, and a painful tender bubo. In 50% of all cases of bubonic plague, a fulminant bacteremic stage develops within 3-5 days of the first onset of symptoms resulting in prostration, shock, delirium and excitus lethalis (Inglesby et al., 2000). The course of pneumonic plague is even more fulminant; after infection, clinical symptoms may be absent until the final day of illness, which may be as early as three days after infection (Inglesby et al., 2000). These patients present with respiratory distress, a copius bloody, frothy sputum and, if untreated, will rarely survive longer than three days (Inglesby et al., 2000). Since the case fatality rate is 50% for bubonic and about 100% for pneumonic plague, treatment must be initiated immediately (Inglesby et al., 2000). Streptomycin is injected in two doses for 10 days; relapses or resistances virtually do not occur, unless drug-resistant strains are the causative agents of disease. If streptomycin cannot be administered, tetracycline is the drug of choice. Patients with plague meningitis must be treated with chloramphenicol. Early drug therapy can reduce the mortality rate of bubonic plague caused by drug-sensitive strains to 11% and that of pneumonic plague to 33%. Pneumonic plague can rarely be controlled beyond 12 hours of fever (Inglesby et al., 2000) Cases of drug-resistant plague infections have been reported and biological warfare industries in the former Soviet Union are believed to have generated *Y. pestis* strains resistant against streptomycin, tetracycline, chloramphenicol and ciprofloxacin (Inglesby et al., 2000).

A number of *Y. pestis* strains are known and characterized. These include KIM, angola, CO92, M26405, and 91001, GB or any one of many (more than several hundred clinical isolates of *Yersinia pestis*, as is described in Anisimov, et al., 2004, which is hereby incorporated by reference). The sequences of the LcrV proteins from these strains are provided in FIG. 1, which also shows their alignment. These different LcrV proteins are nearly identical, with exceptions noted in the figure. The invention extends to different strains of *Y. pestis* and their LcrV proteins. In certain embodiments, a modified LcrV protein will have deleted one or amino acids that is considered to be conserved among the strains. However, it is also contemplated that a nonconserved amino acid can be deleted.

Some, but not all, bubonic plague victims survive the disease even without therapy and appear to develop immunity (Burrows, 1963; Wake et al., 1978). Burrows discovered *Y. pestis* LcrV as a protective antigen, stimulating humoral immune responses in experimental animals that afford protection against plague infection (Burrows, 1956; Burrows, 1957). Based on these observations, several laboratories developed recombinant LcrV subunit vaccines, either alone or in combination with other *Y. pestis* proteins, and demonstrated that a humoral immune response to LcrV confers plague protection in experimental animals (Une and Brubaker, 1984; Motin et al., 1994; Motin et al., 1996; Heath et al., 1998; Anderson et al., 1996; Leary et al., 1995). Brubaker and colleagues first showed that LcrV injection in animals stimulates the release of IL-10, a cytokine that suppresses innate immune functions (Nakajima et al., 1995; Brubaker, 2003). LcrV injection also prevents release of pro-inflammatory cytokines, such as IFN-γ or TNF-α, during plague or other bacterial infections (Nakajima et al., 1995). Recent results suggest that the immune modulatory properties of LcrV involve signaling functions of TLR2 and CD14, imposing systemic suppression of innate immune functions that prohibit the use of LcrV as a plague vaccine in humans (Sing et al., 2002a; Sing et al., 2002b; Sing et al., 2003).

LcrV is secreted via the type III pathway of *Y. pestis* in massive amounts during infection, and mutations that abrogate bacterial expression of LcrV or the type III machinery render *Yersinia* variants avirulent (Burrows, 1956; Skrzypek and Straley, 1995). PcrV, the *Pseudomonas aeruginosa* homolog of LcrV, is also secreted during infection and can be exploited as a protective antigen to prevent Pseudomonas lung infections (Sawa et al., 1999. In contrast to LcrV secreted by pathogenic *Yersinia* spp. (*Y. enterocolitica, Y pseudotuberculosis* and *Y. pestis*) (Brubaker, 2003; Bergmann et al., 1991), PcrV neither activates IL-10 release nor prevents pro-inflammatory cytokine responses during infection, suggesting that the immune modulatory and protective antigen properties of LcrV may represent separable entities (see FIG. 1 and Table 1 for a comparison of *Yersinia* LcrV and *Pseudomonas* PcrV). To test this hypothesis, we generated small deletions in LcrV and examined purified recombinant variants for their immune modulatory properties.

Heesemann and colleagues tested whether synthetic peptides derived from the LcrV sequence were sufficient to stimulate immune responses of CD14/TLR2 co-transfected HEK293 cells and identified peptide V7 (LcrV residues 31-49: VLEELVQLVKDKKIDISIK—SEQ ID NO:7), which is almost completely conserved in *Yersinia* LcrV but absent from *Pseudomonas* PcrV (FIG. 2) (Sing et al., 2002b). The authors reported also that C-terminal truncations of LcrV, including residues 271-300 identified here, retained the ability to induce IL-10 release or suppress TNF-α secretion in C3H/HeJ peritoneal macrophages in a CD14/TLR2 dependent manner (Sing et al., 2002b; Kopp and Medzhitov, 2002).

B. Other *Yersinia* Bacteria and Pathogenicity

The present invention concerns other pathogenic *Yersinia* species, such as *Y. enterocolitica* and *Y. pseudotuberculosis*, all of which require LcrV for human or animal infectious disease. *Y. enterocolitica* is most frequently the cause of Yersiniosis, which can also be caused by other *Yersinia* species. This is an infection that can result in fever, abdominal pain, fever, diarrhea and vomiting. *Y. pseudotuberculosis* is the least common of the three main species of *Yersinia*, causing gastroenteritis as well and has been associated with foodborne infection.

A complication of infection is bacteremia. Consequently, in some embodiments, infection is treated with methods and compositions of the invention involving a modified LcrV polypeptide. It is contemplated that a modified LcrV polypeptide may be employed in post-exposure therapy to provide neutralizing activity against the *Yersinia* pathogen by eliciting an immune response.

The alignment of the *Y. pestis* LcrV protein sequences with these other *Yersinia* species is provided in FIG. 1. This figure shows LcrV is well conserved among the different species. Moreover, it shows that one can readily identify which amino acids of a specific LcrV protein correspond to a particular region identified in the KIM strain (see Examples).

C. Modified LcrV Proteins

In some embodiments, methods and compositions of the present invention concern modified LcrV proteinaceous compositions. These modified LcrV proteins have deletions, insertions, and/or substitutions. In particular embodiments, these modified LcrV proteins are capable of eliciting an immune response in a subject, yet they do not suppress the immune system as much as an unmodified LcrV protein.

Figure 8:
FIG. 8. Amino acid residues 271-300 are positioned in the C-terminal helix of LcrV. Three dimensional model of LcrV as reported (Derewenda et al., 2004) with residues 274-300 are darkened. Residues 1-27, 48-60, 89-90, and 263-273 were omitted because no interpretable electron density was observed in the crystallographic structure (Derewenda et al., 2004). The ribbon diagram was generated with DeepView PDB in conjunction with POV-Ray software (Guex and Peitsch, 1997).

FIG. 8 displays the three dimensional structure of LcrV and the position of amino acids 271-300 within the C-terminal α-12 helix, engaged in a helical coiled-coil with α-7 that together connect the N- and C-terminal globular domains of LcrV (Derewenda et al., 2004; Nilles, 2004). As used herein, a "protein" or "polypeptide" refers to a molecule comprising at least ten amino acid residues. In some embodiments, a wild-type version of a protein or polypeptide are employed, however, in many embodiments of the invention, a modified protein or polypeptide is employed to generate an immune response without the same level of immunosuppressing activity as the unmodified version of the protein. The terms described above may be used interchangeably herein. A "modified protein" or "modified polypeptide" refers to a protein or polypeptide whose chemical structure, particularly its amino acid sequence, is altered with respect to the wild-type protein or polypeptide. In some embodiments, a modified protein or polypeptide has at least one modified activity or function (recognizing that proteins or polypeptides may have multiple activities or functions). The modified activity or function may be reduced immunosuppressive activity. It is specifically contemplated that a modified protein or polypeptide may be altered with respect to one activity or function yet retain wild-type activity or function in other respects, such as immunogenicity.

In certain embodiments the size of a modified protein or polypeptide may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 or greater amino molecule residues, and any range derivable therein. It is contemplated that polypeptides may be mutated by truncation, rendering them shorter than their corresponding wild-type form, but also they might be altered by fusing or conjugating a heterologous protein sequence with a particular function (e.g., for targeting or localization, for enhanced immunogenicity, for purification purposes, etc.).

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (on the World Wide Web at ncbi.nlm.nih.gov/). The coding regions for these known genes may be amplified and/or expressed using the techniques disclosed herein or as would be know to those of ordinary skill in the art.

1. Functional Aspects

When the present application refers to the function or activity of an LcrV protein, it is meant to refer to the activity or function of an unmodified LcrV polypeptide under physiological conditions, unless otherwise specified. For example, an LcrV polypeptide is a particular protein secreted by Yersinia bacteria upon infection. The polypeptide is known 1) to be immunogenic, 2) to suppress the immune system; and 3) prevent release of pro-inflammatory cytokines Determination of which molecules possess any of these activities may be achieved using assays familiar to those of skill in the art.

2. Modified Polypeptides

Amino acid sequence variants of LcrV polypeptides can be substitutional, insertional or deletion variants. A modification in an LcrV polypeptide may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500 or more non-contiguous or contiguous amino acids of the polypeptide, as compared to wild-type. An LcrV polypeptide from any Yersinia species and strain can be used in methods of the invention. Modifications can be made particularly, in some embodiments, in SEQ ID NO:1 through SEQ ID NO:6.

Deletion variants lack one or more residues of the native or wild-type protein. Individual residues can be deleted or a number of contiguous amino acids can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of one or more residues. Terminal additions, called fusion proteins, may also be generated.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a non-polar or uncharged amino acid, and vice versa.

Modified LcrV proteins may be recombinant, or they may be synthesized in vitro. Alternatively the protein may be isolated as a naturally occurring variant. Such proteins may be spontaneous, naturally occurring variants that are isolated. It is also contemplated that a bacteria containing such a variant may be implemented in compositions and methods of the invention. Consequently, a protein need not be isolated.

The term "functionally equivalent codon" is used herein to refer to codons that encode the same amino acid, such as the six codons for arginine or serine, and also refers to codons that encode biologically equivalent amino acids (see Table 1, below).

TABLE 1

Codon Table

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |

TABLE 1-continued

Codon Table

| Amino Acids | | | Codons | | | | | |
|---|---|---|---|---|---|---|---|---|
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2) glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is useful, those that are within ±1 are also useful, as are those within ±0.5.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

It is contemplated that in compositions of the invention, there is between about 0.001 mg and about 10 mg of total protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (orany range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 % maybe modified LcrV protein.

3. Modified Proteins and Epitopic Core Sequences

The present invention contemplates the administration of modified LcrV polypeptides or peptides to effect a preventative therapy against the development of a disease or condition associated with infection by a *Yersinia* pathogen.

Modified LcrV polypeptides corresponding to one or more antigenic determinants of a an unmodified LcrV polypeptide or having "epitopic core regions" can readily be characterized and prepared as discussed in the Examples.

In addition, U.S. Pat. No. 4,554,101 (Hopp), which is incorporated herein by reference, teaches the identification and preparation of epitopes from primary amino acid sequences on the basis of hydrophilicity. Through the methods disclosed in Hopp, one of skill in the art would be able to identify potential epitopes from within an amino acid sequence and then test them.

Numerous scientific publications have also been devoted to the prediction of secondary structure and to the identification of epitopes, from analyses of amino acid sequences (Chou &

Fasman, 1974a,b; 1978a,b, 1979). Any of these may be used, if desired, to supplement the teachings of Hopp in U.S. Pat. No. 4,554,101.

Moreover, computer programs are currently available to assist with predicting antigenic portions and epitopic core regions of proteins. Examples include those programs based upon the Jameson-Wolf analysis (Jameson & Wolf, 1998; Wolf, 1988), the program PepPlot® (Brutlag, 1990; Weinberger, 1985), and other new programs for protein tertiary structure prediction (Fetrow & Bryant, 1993). Further commercially available software capable of carrying out such analyses is termed MacVector(D (IBI, New Haven, Conn.).

4. Protein Production a) Synthetic Proteins

The present invention describes non-native LcrV proteins for use in various embodiments of the present invention. For example, specific polypeptides are assayed for their abilities to elicit an immune response but not have an effect on different cytokines to the same extent as an unmodified and full-length LcrV protein. In specific embodiments, the proteins of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Alternatively, recombinant DNA technology may be employed wherein a nucleotide sequence which encodes a peptide of the invention is inserted into an expression vector, transformed or transfected into an appropriate host cell and cultivated under conditions suitable for expression.

The compositions of the invention may include a polypeptide modified to render it biologically protected. Biologically protected polypeptides have certain advantages over unprotected polypeptides when administered to human subjects and, as disclosed in U.S. Pat. No. 5,028,592, incorporated herein by reference, protected polypeptides often exhibit increased pharmacological activity.

Compositions for use in the present invention may also comprise peptides which include all L-amino acids, all D-amino acids, or a mixture thereof. The use of D-amino acids may confer additional resistance to proteases naturally found within the human body and are less immunogenic and can therefore be expected to have longer biological half lives.

b) In Vitro Protein Production

Following transduction with a vector according to some embodiments of the present invention, primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshney, 1992).

One embodiment of the foregoing involves the use of gene transfer to immortalize cells for the production and/or presentation of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Another embodiment of the present invention uses autologous B lymphocyte cell lines, which are transfected with a viral vector that expresses an immunogene product, and more specifically, a protein having immunogenic activity. Other examples of mammalian host cell lines include Vero and HeLa cells, other B- and T-cell lines, such as CEM, 721.221, H9, Jurkat, Raji, etc., as well as cell lines of Chinese hamster ovary, W138, BHK, COS-7, 293, HepG2, 3T3, RIN and MDCK cells. In addition, a host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection: for dhfr, which confers resistance to trimethoprim and methotrexate; gpt, which confers resistance to mycophenolic acid; neo, which confers resistance to the aminoglycoside G418; and hygro, which confers resistance to hygromycin.

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

II. LcrV-ENCODING NUCLEIC ACID MOLECULES

A. Polynucleotides Encoding Modified Proteins

The present invention concerns recombinant polynucleotides encoding modified LcrV proteins or polypeptides. The nucleic acid sequences for some wild-type LcrV proteins include S38727, M57893, BX936399 (*Yersinia pseudotuberculosis*); AFO53946, AF074612, AE017043, AL117189, M26405 (*Yersinia pestis*); and AF102990, AF336309, NC 004564 (*Yersinia enterocolitis*), all of which are incorporated by reference and can be used to prepare a modified LcrV protein of the invention.

As used in this application, the term "polynucleotide" refers to a nucleic acid molecule that either is recombinant or has been isolated free of total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be RNA, DNA, analogs thereof, or a combination thereof.

In this respect, the term "gene" is used for simplicity to refer to a functional protein, polypeptide, or peptide-encoding unit (including any sequences required for proper transcription, post-translational modification, or localization). As will be understood by those in the art, this functional term includes genomic sequences, cDNA sequences, and smaller engineered gene segments that express, or may be adapted to express, proteins, polypeptides, domains, peptides, fusion proteins, and mutants. A nucleic acid encoding all or part of a native or modified polypeptide may contain a contiguous nucleic acid sequence encoding all or a portion of such a polypeptide of the following lengths: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs.

It also is contemplated that a particular polypeptide from a given species may be represented by natural variants that have slightly different nucleic acid sequences but, nonetheless, encode the same protein (see Table 1 above).

In particular embodiments, the invention concerns isolated DNA segments and recombinant vectors incorporating DNA sequences that encode a modified LcrV protein. Thus, an isolated DNA segment or vector containing a DNA segment may encode, for example, a modified LcrV protein that is immunogenic but is less immunosuppressant compared to the cognate LcrV protein (protein sequence from which it was derived). The term "recombinant" may be used in conjunction with a polypeptide or the name of a specific polypeptide, and this generally refers to a polypeptide produced from a nucleic acid molecule that has been manipulated in vitro or that is the replicated product of such a molecule.

In other embodiments, the invention concerns isolated DNA segments and recombinant vectors incorporating DNA sequences that encode a modified LcrV polypeptide or peptide that can be used to generate an immune response in a subject. These composition can be used as DNA vaccines in some embodiments of the invention.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. In some cases, a nucleic acid sequence may encode a polypeptide sequence with additional heterologous coding sequences, for example to allow for purification of the polypeptide, transport, secretion, post-translational modification, or for therapeutic benefits such as targetting or efficacy. As discussed above, a tag or other heterologous polypeptide may be added to the modified polypeptide-encoding sequence, wherein "heterologous" refers to a polypeptide that is not the same as the modified polypeptide.

The polynucleotides used in the present invention encompass modified LcrV polypeptides and peptides that may be biologically and functionally equivalent in some aspects to an unmodified LcrV protein but different in others. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity of the protein, to decrease immunosuppression caused by the protein, to reduce toxicity effects of the protein in vivo to a subject given the protein, or to increase the efficacy of any treatment involving the protein.

In certain other embodiments, the invention concerns isolated DNA segments and recombinant vectors that include within their sequence a contiguous nucleic acid sequence from that shown in sequences identified herein (and/or incorporated by reference). Such sequences, however, may be modified to yield a protein product whose activity is altered with respect to wild-type, as discussed herein.

It also will be understood that this invention is not limited to the particular nucleic acid and amino acid sequences of these identified sequences.

In particular embodiments, the invention concerns modified LcrV proteins that have a deletion of one or more amino acids compared to the unmodified LcrV protein. Deletions may be internal deletions (not encompassing the amino acid at either the 5' or 3' end) or they may be terminal deletions. In some cases, a modified LcrV may have multiple regions deleted, including internal and/or terminal regions. Such deletions can be readily constructed by the skilled artisan, including by the methods described in the Examples.

The present invention also concerns DNA vaccines. The vehicle for a DNA segment encoding a protein against which an immune response is desired is well established. Such a vehicle often contains unmethylated immunostimulatory CpG-S motifs, such as those described in U.S. Pat. No. 6,821, 957, which is hereby incorporated by reference. These motifs serve as a self-adjuvant, and such a polynucleotide can be used with or without other adjuvants, which are discussed infra.

B. Vectors

Modified LcrV polypeptides may be encoded by a nucleic acid molecule comprised in a vector. The term "vector" is used to refer to a carrier nucleic acid molecule into which an exogenous nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., (2001) and Ausubel et al., 1996, both incorporated herein by reference. In addition to encoding a modified LcrV polypeptide, a vector may encode non-LcrV polypeptide sequences such as a tag or targeting molecule. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage. A targeting molecule is one that directs the modified polypeptide to a particular organ, tissue, cell, or other location in a subject's body.

Vectors of the invention may be used in a host cell to produce a modified LcrV polypeptide that may subsequently be purified for administration to a subject or the vector may be purified for direct administration to a subject for expression of the protein in the subject.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it may be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (2001), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Table 2 lists several elements/promoters that may be employed, in the context of the present invention, to regulate the expression of a gene. This list is not intended to be exhaustive of all the possible elements involved in the promotion of expression but, merely, to be exemplary thereof. Table 3 provides examples of inducible elements, which are regions of a nucleic acid sequence that can be activated in response to a specific stimulus.

TABLE 2

| Promoter and/or Enhancer | |
|---|---|
| Promoter/Enhancer | References |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al,, 1986; Imbra et al., 1986; Kadesch et al., 1986; Wang et al., 1986; Ondek et al., 1987; Kuhl et al., 1987; Schaffner et al., 1988 |

TABLE 2-continued

Promoter and/or Enhancer

| Promoter/Enhancer | References |
| --- | --- |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell et al., 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) IE | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
| --- | --- | --- |
| MT II | Phorbol Ester (TFA) Heavy metals | Palmiter et al., 1982; Haslinger et al., 1985; Searle et al., 1985; Stuart et al., 1985; Imagawa et al., 1987; Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Also contemplated as useful in the present invention are the dectin-1 and dectin-2 promoters. Additional viral promoters, cellular promoters/enhancers and inducible promoters/enhancers that could be used in combination with the present invention are listed in Tables 2 and 3. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

The particular promoter that is employed to control the expression of a modified LcrV polynucleotide is not believed to be critical, so long as it is capable of expressing the polynucleotide in a targeted cell. Thus, where a human cell is targeted, it is contemplated that one would position the polynucleotide coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, and the Rous sarcoma virus long terminal repeat can be used to obtain high-level expression of the modified LcrV polynucleotide. The use of other viral or mammalian cellular or bacterial phage promoters, which are well-known in the art, to achieve expression of polynucleotides is contemplated as well, provided that the levels of expression are sufficient to induce an immune response.

In embodiments in which a vector is administered to a subject for expression of the protein, it is contemplated that a desirable promoter for use with the vector is one that is not down-regulated by cytokines or one that is strong enough that even if down-regulated, it produces an effective amount of the modified LcrV protein in a subject to elicit an immune response against LcrV. Examples of these are CMV IE and RSV LTR. In other embodiments, a promoter that is up-regulated in the presence of cytokines is employed. The MHC I promoter increases expression in the presence of IFN-γ.

Tissue specific promoters can be used, particularly if expression is in cells in which expression of an antigen is desirable, such as dendritic cells or macrophages. The mammalian MHC I and MHC II promoters are examples of such tissue-specific promoters.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5'- methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Samow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, incorporated herein by reference.)

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, the terminator may comprise a signal for the cleavage of the RNA, and it may be the case that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Certain embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

D. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors or viruses (which does not qualify as a vector if it expresses no exogenous polypeptides). A host cell may be "transfected" or "transformed," which refers to a process by which exogenous nucleic acid, such as a modified protein-encoding sequence, is transferred or introduced into the host cell. A transformed cell includes the primary subject cell and its progeny.

Host cells may be derived from prokaryotes or eukaryotes, including yeast cells, insect cells, and mammalian cells, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla, Calif.). Alternatively, bacterial cells such as *E. coli* LE392 could be used as host cells for phage viruses. Appropriate yeast cells include *Saccharomyces cerevisiae, Saccharomyces pombe*, and *Pichia pastoris*.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

E. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

F. Amplification of Nucleic Acids

Nucleic acids used as a template for amplification may be isolated from cells, tissues or other samples according to standard methodologies (Sambrook et al., 2001). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is often employed.

Pairs of primers designed to selectively hybridize to nucleic acids corresponding to sequences of genes identified herein are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

Alternative methods for amplification of target nucleic acid sequences that may be used in the practice of the present invention are disclosed in U.S. Pat. Nos. 5,843,650, 5,846, 709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

G. Methods of Gene Transfer

Suitable methods for nucleic acid delivery to effect expression of compositions of the present invention are believed to include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981, 274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

III. IMMUNE RESPONSE ASSAYS

As discussed above, the invention concerns evoking an immune response in a subject against an LcrV protein. In one embodiment, the immune response can protect the subject against infection or disease.

A. Immunoassays

The present invention includes the implementation of serological assays to evaluate whether and to what extent an immune response is induced or evoked by LcrV proteins of the invention. There are many types of assays that can be implemented, which one of ordinary skill in the art would know how to implement in the scope of the present invention. Examples are included below.

Immunoassays encompassed by the present invention include, but are not limited to, those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

Immunoassays generally are binding assays. Certain useful immunoassays are the various types of enzyme linked immunosorbent assays (ELISAs) and radioimmunoassays (RIA) known in the art. Immunohistochemical detection using tissue sections is also particularly useful.

In one exemplary ELISA, the antibodies are immobilized on a selected surface, such as a well in a polystyrene microtiter plate, dipstick, or column support. Then, a test composition suspected of containing the desired antigen, such as a clinical sample, is added to the wells. After binding and washing to remove non-specifically bound immune complexes, the bound antigen may be detected. Detection is generally achieved by the addition of another antibody, specific for the desired antigen, that is linked to a detectable label. This type of ELISA is known as a "sandwich ELISA". Detection also may be achieved by the addition of a second antibody specific for the desired antigen, followed by the addition of a third antibody that has binding affinity for the second antibody, with the third antibody being linked to a detectable label.

Variations on ELISA techniques are known to those of skill in the art. In one such variation, the samples suspected of containing the desired antigen are immobilized onto the well surface and then contacted with the antibodies of the invention. After binding and appropriate washing, the bound immune complexes are detected. Where the initial antigen specific antibodies are linked to a detectable label, the immune complexes may be detected directly. Again, the immune complexes may be detected using a second antibody that has binding affinity for the first antigen specific antibody, with the second antibody being linked to a detectable label.

Competition ELISAs are also possible in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal.

Irrespective of the format employed, ELISAs have certain features in common, such as coating, incubating or binding, washing to remove non-specifically bound species, and detecting the bound immune complexes. These are described as below.

Antigen or antibodies may also be linked to a solid support, such as in the form of plate, beads, dipstick, membrane, or column matrix, and the sample to be analyzed is applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely-adsorbed material. Any remaining available surfaces of the wells are then "coated" with a nonspecific protein that is antigenically neutral with regard to the test antisera. These include bovine serum albumin (BSA), casein, and solutions of milk powder. The coating allows for blocking of nonspecific adsorption sites on the immobilizing surface and thus reduces the background caused by nonspecific binding of antisera onto the surface.

In ELISAs, it is more customary to use a secondary or tertiary detection means rather than a direct procedure. Thus, after binding of the antigen or antibody to the well, coating with a non-reactive material to reduce background, and washing to remove unbound material, the immobilizing surface is contacted with the clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions typically include diluting the antigens and antibodies with solutions such as BSA, bovine gamma globulin (BGG) and phosphate buffered saline (PBS)/TWEEN (polysorbate). These added agents also tend to assist in the reduction of nonspecific background.

The suitable conditions also mean that the incubation is at a temperature and for a period of time sufficient to allow effective binding. Incubation steps are typically from about 1 to 2 to 4 hours, at temperatures that may be on the order of 25° to 27° C., or may be overnight at about 4° C. or so.

After all incubation steps in an ELISA are followed, the contacted surface is washed so as to remove non-complexed material. Washing often includes washing with a solution of PBS/TWEEN™, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. In some embodiments, this will be an enzyme that will generate color development upon incubating with an appropriate chromogenic substrate. Thus, for example, one will desire to contact and incubate the first or second immune complex with a urease, glucose oxidase, alkaline phosphatase, or hydrogen peroxidase-conjugated antibody for a period of time and under conditions that favor the development of further immune complex formation, e.g., incubation for 2 hours at room temperature in a PBS-containing solution such as PBS-TWEEN™.

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

Alternatively, the label may be a chemiluminescent one. The use of such labels is described in U.S. Pat. Nos. 5,310,687, 5,238,808 and 5,221,605.

B. Protective Immunity

In some embodiments of the invention, proteinaceous modified LcrV compositions confer protective immunity on a subject. Protective immunity refers to a body's ability to mount a specific immune response that protects the subject from developing a particular disease or condition that involves the agent against which there is an immune response. An immunogenically effective amount is capable of conferring protective immunity to the subject.

IV. TREATMENT METHODS

A method of the present invention includes treatment for a disease or condition caused by a *Yersinia* pathogen. An immunogenic LcrV polypeptide of the invention can be given to induce an immune response in a person infected with a *Yersinia* pathogen or suspected of having been exposed to a *Yersinia* pathogen. Methods may be employed with respect to individuals who have tested positive for exposure to a *Yersinia* pathogen or who are deemed to be at risk for infection based on possible exposure.

Other therapeutic methods of the invention include employing an immunosuppressing LcrV protein as an immunosuppressant agent in a subject who is in need or is suspected to be in need of an immunosuppressant. In particular embodiments, the subject has been diagnosed with, has symptoms of, or is at risk for an autoimmune disease, graft versus host disease or organ transplant rejection.

In some embodiments, the treatment is administered in the presence of adjuvants or carriers or other *Yersinia pestis* antigens. Furthermore, in some examples, treatment comprises administration of other agents commonly used against bacterial infection, such as an antibiotic.

The use of peptides for vaccination typically requires conjugation of the peptide to an immunogenic carrier protein, such as hepatitis B surface antigen, keyhole limpet hemocyanin or bovine serum albumin. Methods for performing this conjugation are well known in the art.

V. Pharmaceutical Compositions and Routes of Administration

The present invention includes compositions that can be used to induce an immune response against an LcrV polypeptide so as to protect against infection by a *Yersinia* pathogen and against developing a condition or disease caused by such a pathogen.

In some embodiments, pharmaceutical compositions are administered to a subject. Different aspects of the present invention involve administering an effective amount of a composition that includes a non-native LcrV protein to a subject. In some embodiments of the present invention, LcrV polypeptides or peptides may be administered to the patient to protect against infection by one or more *Yersinia* pathogens. Alternatively, an expression vector encoding such polypeptides or peptides may be given to a patient as a preventative treatment. Additionally, such compounds can be administered in combination with an antibiotic.

In other embodiments, a modified LcrV polypeptide is used as an immunosuppressant for indications in which immunosuppression is desirable. In these embodiments, it is contemplated that compositions and methods can involve other immunosuppressants, such as corticosteroids.

Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including cremes, lotions, mouthwashes, inhalants and the like.

The active compounds of the present invention can be formulated for parenteral administration, e.g., formulated for injection via the intravenous, intramuscular, sub-cutaneous, or even intraperitoneal routes. The preparation of an aqueous composition that contains a compound or compounds that increase the expression of an MHC class I molecule will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be desirable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, commonly employed methods of preparation include vacuum-drying and freeze-drying techniques, which yield a powder of the active ingredient, plus any additional desired ingredient from a previously sterile-filtered solution thereof.

In certain cases, the therapeutic formulations of the invention also may be prepared in forms suitable for topical administration, such as in cremes and lotions. These forms may be used for treating skin-associated diseases, such as various sarcomas.

Administration of therapeutic compositions according to the present invention will be via any common route so long as the target tissue is available via that route. This includes oral, nasal, buccal, rectal, vaginal, mucosal, or topical. Alternatively, administration will be by orthotopic, intradermal, subcutaneous, intramuscular, intraperitoneal, intravaginal, intranasal, or intravenous injection. In certain embodiments, the vaccine is inhaled (e.g., U.S. Pat. No. 6,651,655, which is specifically incorporated by reference). Volume of the aerosol is between about 0.01 ml and 0.5 ml. Such compositions would normally be administered as pharmaceutically acceptable compositions that include physiologically acceptable carriers, buffers or other excipients.

In certain embodiments, it may be desirable to provide a continuous supply of therapeutic compositions for a period of time to the patient. The time frame includes administration for one or more hours, one or more days, one or more weeks, or one or more months, with a possible hiatus during that time period. For intravenous or intraarterial routes, this is accomplished by drip system. For topical applications, repeated application would be employed. For various approaches, delayed release formulations could be used that provided limited but constant amounts of the therapeutic agent over an extended period of time. For internal application, continuous perfusion, for example with a modified LcrV protein may be preferred. This could be accomplished by catheterization, post-operatively in some cases, followed by continuous administration of the therapeutic agent. The time period for perfusion would be selected by the clinician for the particular patient and situation, but times could range from about 1-2 hours, to 2-6 hours, to about 6-10 hours, to about 10-24 hours, to about 1-2 days, to about 1-2 weeks or longer. Generally, the dose of the therapeutic composition via continuous perfusion will be equivalent to that given by single or multiple injections, adjusted for the period of time over which the injections are administered. It is believed that higher doses may be achieved via perfusion, however.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, Remington's Pharmaceutical Sciences, 1990). Some variation in dosage will necessarily occur depending on the condition of the subject being treated. The person responsible for administration will, in any event, determine the appropriate dose for the individual subject.

AA effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability, and toxicity of the particular therapeutic substance.

Amounts for particular formulations may be expressed as about, about at least, or about at most 1, 5, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000 µg or mg, or as µM or mM, or any range of number derivable therein.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

A. In Vitro, Ex Vivo, In Vivo Administration

As used herein, the term in vitro administration refers to manipulations performed on cells removed from an animal, including, but not limited to, cells in culture. The term ex vivo administration refers to cells which have been manipulated in vitro, and are subsequently administered to a living animal. The term in vivo administration includes all manipulations performed on cells within an animal.

In certain aspects of the present invention, the compositions may be administered either in vitro, ex vivo, or in vivo. In certain in vitro embodiments, autologous B-lymphocyte cell lines are incubated with a virus vector of the instant invention for 24 to 48 hours or with a modified LcrV polypeptide for two hours. The transduced cells can then be used for in vitro analysis, or alternatively for in vivo administration.

U.S. Pat. Nos. 4,690,915 and 5,199,942, both incorporated herein by reference, disclose methods for ex vivo manipulation of blood mononuclear cells and bone marrow cells for use in therapeutic applications.

B. Vaccines

The present invention includes methods for preventing the development of plague. As such, the invention contemplates vaccines for use in both active and passive immunization embodiments. Immunogenic compositions, proposed to be suitable for use as a vaccine, may be prepared most readily directly from immunogenic modified LcrV polypeptides prepared in a manner disclosed herein. In some cases the antigenic material is extensively dialyzed to remove undesired small molecular weight molecules and/or lyophilized for more ready formulation into a desired vehicle.

Alternatively, other viable and important options for a protein-based vaccine involve introducing the protein sequences as nucleic acids or as direct DNA vaccines. In this regard, recent reports described construction of recombinant vaccinia viruses expressing either 10 contiguous minimal CTL epitopes (Thomson, 1996) or a combination of B cell, CTL, and TH epitopes from several microbes (An, 1997), and successful use of such constructs to immunize mice for priming protective immune responses. Thus, there is ample evidence in the literature for successful utilization of peptides, peptide-pulsed APCs, and peptide-encoding constructs for efficient in vivo priming of protective immune responses, in particular, CMI.

The use of nucleic acid sequences as vaccines is described in U.S. Pat. Nos. 5,958,895 and 5,620,896.

The preparation of vaccines that contain modified LcrV polypeptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables either as liquid solutions or suspensions: solid forms suitable for solution in or suspension in liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants that enhance the effectiveness of the vaccines.

In specific embodiments, vaccines are formulated with a combination of substances, as described in U.S. Pat. Nos. 6,793,923 and 6,733,754, which are hereby incorporated by reference.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, such as about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, such as about 25% to about 70%.

The LcrV-derived polypeptides and LcrV-encoded DNA constructs of the present invention may be formulated into the vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

In many instances, it will be desirable to have multiple administrations of the vaccine, usually not exceeding six vaccinations, more usually not exceeding four vaccinations and often one or more, usually at least about three vaccinations. The vaccinations will normally be at from two to twelve week intervals, more usually from three to five week intervals. Periodic boosters at intervals of 1-5 years, usually three years, will be desirable to maintain protective levels of the antibodies. The course of the immunization may be followed by assays for antibodies for the supernatant antigens. Boosters or subsequent vaccinations may be with the same or different amounts of the antigen as the initial vaccine or with respect to each other. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays.

1. Carriers

As is well known in the art, a given composition may vary in its immunogenicity. It is often necessary therefore to boost the host immune system, as may be achieved by coupling the modified LcrV polypeptide immunogen to a carrier. Exemplary carriers are keyhole limpet hemocyanin (KLH) and bovine serum albumin (BSA). Other albumins such as ovalbumin, mouse serum albumin, or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde, and bis-biazotized benzidine.

2. Adjuvants

As is also well known in the art, the immunogenicity of HIV polypeptide or peptide composition can be enhanced by the use of non-specific stimulators of the immune response, known as adjuvants. Suitable adjuvants include all acceptable immunostimulatory compounds, such as cytokines, toxins, or synthetic compositions.

A number of adjuvants can be used to enhance an antibody response against a modified LcrV protein. Adjuvants can 1) trap the antigen in the body to cause a slow release; 2) attract cells involved in the immune response to the site of administration; 3) to induce proliferation and/or activation of immune system cells; and/or 4) improve the spread of the antigen throughout the subject's body.

Adjuvants include, but are not limited to, oil-in-water emulsions, water-in-oil emulsions, mineral salts, polynucleotides, and natural substances. Specific adjuvants that may be used include IL-1, IL-2, IL-4, IL-7, IL-12, γ-interferon, GMCSP, BCG, aluminum hydroxide or other aluminum compound, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion. MHC antigens may even be used. Others can be found in U.S. Pat. Nos. 6,814,971, 5,084,269, 6,656,462, and which also teach how to make and use such compounds (these patents are herein incorporated by reference).

Various methods of achieving adjuvant effect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin-treated (Fab) antibodies to albumin, mixture with bacterial cells such as C. parvum or endotoxins or lipopolysaccharide components of Gram-negative bacteria, emulsion in physiologically acceptable oil vehicles such as mannide mono-oleate (Aracel A), or emulsion with a 20% solution of a perfluorocarbon (Fluosol-DA®) used as a block substitute may also be employed.

Exemplary adjuvants include complete Freund's adjuvant (a non-specific stimulator of the immune response containing killed Mycobacterium tuberculosis), incomplete Freund's adjuvants and aluminum hydroxide adjuvant.

In addition to adjuvants, it may be desirable to coadminister biologic response modifiers (BRM), which have been shown to upregulate T cell immunity or downregulate suppresser cell activity. Such BRMs include, but are not limited to, Cimetidine (CIM; 1200 mg/d) (Smith/Kline, Pa.); or low-dose Cyclophosphamide (CYP; 300 mg/m$^2$) (Johnson/ Mead, N.J.) and cytokines such as γ-interferon, IL-2, or IL-12 or genes encoding proteins involved in immune helper functions, such as B-7.

C. Lipid Components and Moieties

In certain embodiments, the present invention concerns compositions comprising one or more lipids associated with a nucleic acid or an amino acid molecule. A lipid is a substance that is characteristically insoluble in water and extractable with an organic solvent. Compounds other than those specifically described herein are understood by one of skill in the art as lipids, and are encompassed by the compositions and methods of the present invention. A lipid component and a non-lipid may be attached to one another, either covalently or non-covalently.

A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof.

A nucleic acid molecule or amino acid molecule, such as a peptide, associated with a lipid may be dispersed in a solution containing a lipid, dissolved with a lipid, emulsified with a lipid, mixed with a lipid, combined with a lipid, covalently bonded to a lipid, contained as a suspension in a lipid or otherwise associated with a lipid. A lipid or lipid/poxvirus-associated composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine(Gibco BRL)-poxvirus or Superfect (Qiagen)-poxvirus complex is also contemplated.

In certain embodiments, a lipid composition may comprise about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or any range derivable therein, of a particular lipid, lipid type or non-lipid component such as a drug, protein, sugar, nucleic acids or other material disclosed herein or as would be known to one of skill in the art. In a non-limiting example, a lipid composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a drug. Thus, it is contemplated that lipid compositions of the present invention may comprise any of the lipids, lipid types or other components in any combination or percentage range.

D. Combination Therapy

Of course it is understood that the method of the present invention, particularly administration of a modified LcrV protein to a patient, may also be used in combination with the administration of traditional therapies. These include, but are not limited to, the administration of antibiotics such as streptomycin, ciprofloxacin, doxycycline, gentamycin, chloramphenicol, trimethoprim, sulfamethoxazole, ampicillin, or tetracycline.

In one embodiment of the present invention, it is contemplated that a modified LcrV polypeptide vaccine and/or therapy is used in conjunction with antibacterial treatment. Alternatively, the therapy may precede or follow the other agent treatment by intervals ranging from minutes to weeks. In embodiments where the other agent and LcrV protein or polynucleotide are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 h of each other such as within about 6-12 h of each other. In some situations, it may be desirable to extend the time period for treatment significantly, however, where several day (2, 3, 4, 5, 6 or 7) to several wk (1, 2, 3, 4, 5, 6, 7 or 8) lapse between the respective administrations.

Various combinations may be employed, for example gene therapy is "A" and the immunogenic molecule given as part of an immune therapy regime, such as an antigen, is "B".

```
A/B/A  B/A/B  B/B/A  A/A/B  A/B/B  B/A/A  A/B/B/B
B/A/B/B  B/B/B/A  B/B/A/B  A/A/B/B  A/B/A/B  A/B/B/A
B/B/A/A  B/A/B/A  B/A/A/B  A/A/A/B  B/A/A/A  A/B/A/A
A/A/B/A
```

Administration of the therapeutic expression constructs of the present invention to a patient will follow general protocols for the administration of such compounds, taking into account the toxicity, if any, of the LcrV composition. It is expected that the treatment cycles would be repeated as necessary. It also is contemplated that various standard therapies, such as hydration, may be applied in combination with the described therapy.

VI. EXAMPLES

The following examples are included to demonstrate certain embodiments of the invention. It should be appreciated by those of skill in the art that the techniques disclosed in the examples which follow represent techniques discovered by the inventor to function well in the practice of the invention, and thus can be considered to constitute some modes for its practice. However, those of skill in the art should, in light of the present disclosure, appreciate that many changes can be made in the specific embodiments which are disclosed and still obtain a like or similar result without departing from the spirit and scope of the invention.

The reference of Overheim et al., 2005 discusses Examples 1-4 and is hereby incorporated by reference with respect to implementing these examples and providing additional information related to these examples.

Example 1

Materials and Methods for Examples 2-4

Construction of rLcrV Expression Vectors

*Y. pestis* strain KIM coding sequence of lcrV was PCR amplified with primers specifying abutted NdeI and BamHI restriction sites. Amplified DNA fragment was cloned into pCR2.1 (Invitrogen), recombinant plasmid was isolated and cloned insertions were verified by DNA sequencing. Inserts containing the correct sequence were excised with NdeI/BamHI cleavage and subcloned into the expression vector pET16b (Novagen) cut with the same enzymes to yield prLcrV. To generate rV1 and rV1 deletions (FIG. 3), lcrV DNA fragments with 5' or 3' truncations were amplified with oligonucleotide primers that annealed at the appropriate sites and harbored either abutted NdeI (5' truncation) or BamHI (3' truncation) restriction sites, respectively. PCR products were cloned into pET16b as described above. To generate internal 30 codon deletions, lcrV was PCR amplified with two primer pairs, generating 5' and 3' coding fragments that were joined by ligation at a unique KpnI restriction site, generated from nucleotide sequences that were abutted to PCR primers. Fragments were amplified by PCR, cloned into pCR2.1 (Invitrogen), excised with restriction enzymes, ligated together and sub-cloned as joined NdeI/BamHI fragments into pET16b. *P. aeruginosa* PcrV was amplified using the same restriction sites and also cloned into pET16b. The primers for all constructs described herein are listed in Table 4.

TABLE 4

Oligonucleotides used for construction of LcrV variants

| Plasmid | Amino Acid Deletion | Forward Primer | Reverse Primer |
|---|---|---|---|
| pEM1 | Δ1-30 AA | AACATATGGTTTTAGAAGAAT TGGTTCAGTT-SEQ ID NO: 8 | AAGGATCCTTTACCAGACG TGTCATC-SEQ ID NO: 9 |
| pEM2 | Δ31-60 AA | AAGGTACCAATAGAGTAATTA CTGATGATATC-SEQ ID NO: 10 | AAGGATCCTTTACCAGACG TGTCATC-SEQ ID NO: 11 |
| pEM3 | Δ61-90 AA | AACATATGATTAGAGCCTACG AACAA-SEQ ID NO: 12 | AAGGTACCGGCAAAAACCT CCGAATCTTT-SEQ ID NO: 13 |
| pEM3 | Δ61-90 AA | AAGGTACCGACAACCAACTGC AAAATGG-SEQ ID NO: 14 | AAGGATCCTTTACCAGACG TGTCATC-SEQ ID NO: 15 |
| pEM4 | Δ91-120 AA | AACATATGATTAGAGCCTACG AACAA-SEQ ID NO: 16 | AAGGTACCATAATGACCGC CTTTAAGAATG-SEQ ID NO: 17 |
| pEM4 | Δ91-120 AA | AAGGTACCGTAATGCATTTCT CTTTAACCG-SEQ ID NO: 18 | AAGGATCCTTTACCAGACG TGTCATC-SEQ ID NO: 19 |

TABLE 4-continued

Oligonucleotides used for construction of LcrV variants

| Plasmid | Amino Acid Deletion | Forward Primer | Reverse Primer |
|---|---|---|---|
| pEM5 | Δ121-150 AA | AACATATGATTAGAGCCTACG AACAA-SEQ ID NO: 20 | AAGGTACCTGCCATGAACG CCCGCAAT-SEQ ID NO: 21 |
| pEM5 | Δ121-150 AA | AAGGTACCAGCAAGTTGCGTG AAGAATTA-SEQ ID NO: 22 | AAGGATCCTTTACCAGACG TGTCATC-SEQ ID NO: 23 |
| pEM6 | Δ151-180 AA | AACATATGATTAGAGCCTACG AACAA-SEQ ID NO: 24 | AAGGTACCACGGGCATCAC CATGATGAT-SEQ ID NO: 25 |
| pEM6 | Δ151-180 AA | AAGGTACCAGTGGCACCATAA ATATCCAT-SEQ ID NO: 26 | AAGGATCCTTTACCAGACG TGTCATC-SEQ ID NO: 27 |
| pEM7 | Δ181-210 AA | AACATATGATTAGAGCCTAGG AACAA-SEQ ID NO: 28 | AAGGTACCACTAGACAGAT GCTTATTAATTT-SEQ ID NO: 29 |
| pEM7 | Δ181-210 AA | AAGGTACCGCAGAGTACAAAA TTCTCGAG-SEQ ID NO: 30 | AAGGATCCTTTACCAGACG TGTCATC-SEQ ID NO: 31 |
| pEM8 | Δ211-240 AA | AACATATGATTAGAGCCTACG AACAA-SEQ ID NO: 32 | AAGGTACCGCTGGCTTTAA AAATCTCTTCA-SEQ ID NO: 33 |
| pEM8 | Δ211-240 AA | AAGGTACCGGAAGTGAGAATA AAAGAACC-SEQ ID NO: 34 | AAGGATCCTTTACCAGACG TGTCATC-SEQ ID NO: 35 |
| pEM9 | Δ241-270 AA | AACATATGATTAGAGCCTACG AACAA-SEQ ID NO: 36 | AAGGTACCAAGAAAGTCCT TTATCGAGACT-SEQ ID NO: 37 |
| pEM9 | Δ241-270 AA | AAGGTACCACCACCTGCTCGG ATAAGT-SEQ ID NO: 38 | AAGGATCCTTTACCAGACG TGTCATC-SEQ ID NO: 39 |
| pEM10 | Δ271-300 AA | AACATATGATTAGAGCCTACG AACAA-SEQ ID NO: 40 | AAGGTACCGGCAAAGTGAG ATAATTCATTAT-SEQ ID NO: 41 |
| pEM11 | Δ301-326 AA | AACATATGATTAGAGCCTACG AACAA-SEQ ID NO: 42 | AAGGATCCTGAATTAAAAC GTGATGTAATATC-SEQ ID NO: 43 |

Expression and Purification of rLcrV and rLcrV Variants

E. coli BL21 (DE3) (Studier et al., 1990) carrying prLcrV or any one of its variants were grown overnight at 37° C. in Luria-Bertani medium with 100 μg/ml ampicillin. Bacteria were diluted into fresh medium and grown to $OD_{600}$ 0.5. T7 polymerase was induced with 1 mM isopropyl-1-thiol-D-galactopyranoside, bacterial growth was continued for three hours at 37° C. and cells were harvested by centrifugation at 10,000×g for 15 min. E. coli cells of 500 ml culture were disrupted twice in a French pressure cell at 14,000 psi in 20 ml of 50 mM Tris-HCl (pH 7.5), 150 mM NaCl (column buffer) containing 100 μM phenylmethylsulfonyl fluoride. Lysate was subjected to ultra-centrifugation at 100,000×g for 30 min, and the soluble fraction was applied to Ni-NTA column (1 ml bed volume), pre-equilibrated with 20 ml column buffer. The column was washed with 20 volumes of the same buffer, followed by a second washing with 20 volumes of column buffer containing 20 mM imidazole. Bound protein was eluted in 50 mM Tris-HCl (pH 7.5), 150 mM NaCl with either 250 mM or 500 mM imidazole. Purified proteins were subjected to Triton-X114 (Sigma) phase separation to remove endotoxin (Aida and Pabst, 1990). Purified proteins were subjected to G25 column (Amersham) to remove residual Triton-X114 and retrieved by phosphate buffered saline (PBS) elution. LPS contamination of protein was assayed with the limulus amebocyte lysate (LAL, QCL-1000, Cambrex, N.J.) and determined to be less than 1 ng per 100 μg purified protein (Sawa et al., 1999). Protein concentrations were determined by BCA assay (Pierce Biotechnology, Rockford, Ill.) or by measuring absorption at 280 nm. Proteins were flash frozen with dry ice and ethanol and stored at −80° C. for further use.

Animal Immunization and Challenge with Y. pestis Strain KIM D27

Groups of 6-8 week old female BALB/c mice (Charles River Labs, MA) were immunized with 50 μg of purified protein, pre-absorbed to adjuvant by mixing with 50 μL 50% v/v ALHYDROGEL™, and injected intra-muscularly into the hind leg. On day 21 following primary immunization, mice were boosted with a second injection of the same antigen with an equal dose. Blood samples were withdrawn via peri-orbital bleeding either before immunization or on day 7, 14, 28, and 42 after primary immunization. Following blood clotting, serum was retrieved from the supernatant of samples centrifuged at 1,000×g and used for measurements of antibody production. Immunized animals were challenged on day 43 by retro-orbital injection with 0.1 ml aliquots of either 10 or 1,000 lethal doses of Y. pestis strain KIM D27 ($1\times10^3$ or $1\times10^5$ colony forming units, cfu) (Brubaker, 1969). For this experiment, Y. pestis KIM D27 was grown in HIB (Heart Infusion Broth) at 37° C. overnight, diluted 1:20 into fresh HIB and grown for 3 hours at 37° C. until the culture reached $OD_{600}$ 1.0. Plague bacilli were washed and diluted into sterile PBS. Animals were anesthetized for this procedure by injecting a cocktail of 17 mg/ml ketamine (Ketsed, Vedco) and 0.7 mg/ml of xylazine (Sigma) intra-peritoneally. Mice were infected by retro-orbital injection with bacterial suspensions and observed for 14 days for the development of disease symptoms and time-to-lethal infection recorded. Serum IgG levels with specific antigen binding activity were determined by custom ELISA in the GLRCE Immunology Core at the University of Chicago.

Macrophage Assays

Peritoneal cavities of 6-8 week old C57BL/6 mice (Jackson Laboratories, Me.) were lavaged with cold, serum free HBSS. Cells were plated in triplicate at a density of $5 \times 10^5$ cells/well, using 48 well dishes and serum free RPMI. After 2 hours of incubation at 37° C. in an atmosphere with 5% $CO_2$, plates were carefully washed 3 times with pre-warmed, serum free media to remove non-adherent cells and fresh RPMI containing 10% fetal calf serum (Gemini Bio-Products, Calif.), 2 mM L-glutamine (Gemini Bio-Products, Calif.), 100 U/ml penicillin (Gemini Bio-Products), 100 U/ml streptomycin (Gemini Bio-Products), and 50 μM β-mercaptoethanol. Greater than 95% of the adherent cell population represented macrophages as determined by morphology and flow cytometric analysis. Macrophage cultures were propagated for two hours with or without 1 μg/ml LPS pre-stimulation. Macrophage preparations were treated with the following reagents: LPS (1 μg/ml), rLcrV (10 μg/ml), rV1-rV11 (10 μg/ml), rPcrV (10 μg/ml) or PBS. Macrophage culture supernatants were collected 18 hours after addition of proteins and analyzed by ELISA for concentration of IL-10 (BD Biosciences, Calif.) and TNF-α (R&D Systems, Minn.) according to the manufacturer's recommendations.

Human Monocytic Cells

Human THP-1 cells (ATCC TIB-202) were cultured in RPMI 1640 supplemented with 0.005 mM 2-mercaptoethanol and 10% fetal bovine serum and incubated at 37° C. in 5% $CO_2$. THP-1 cells were cultured at a density of $5 \times 10^5$ cells/ml and stimulated in triplicate with LPS (1 μg/ml), rLcrV, rV10 or rV11 (10 μg/ml). Culture supernatants were collected after 18 hours of incubation and analyzed by ELISA for IL-10.

Example 2 rLcrV Variants and their Immune Modulatory Properties

Figure 4:
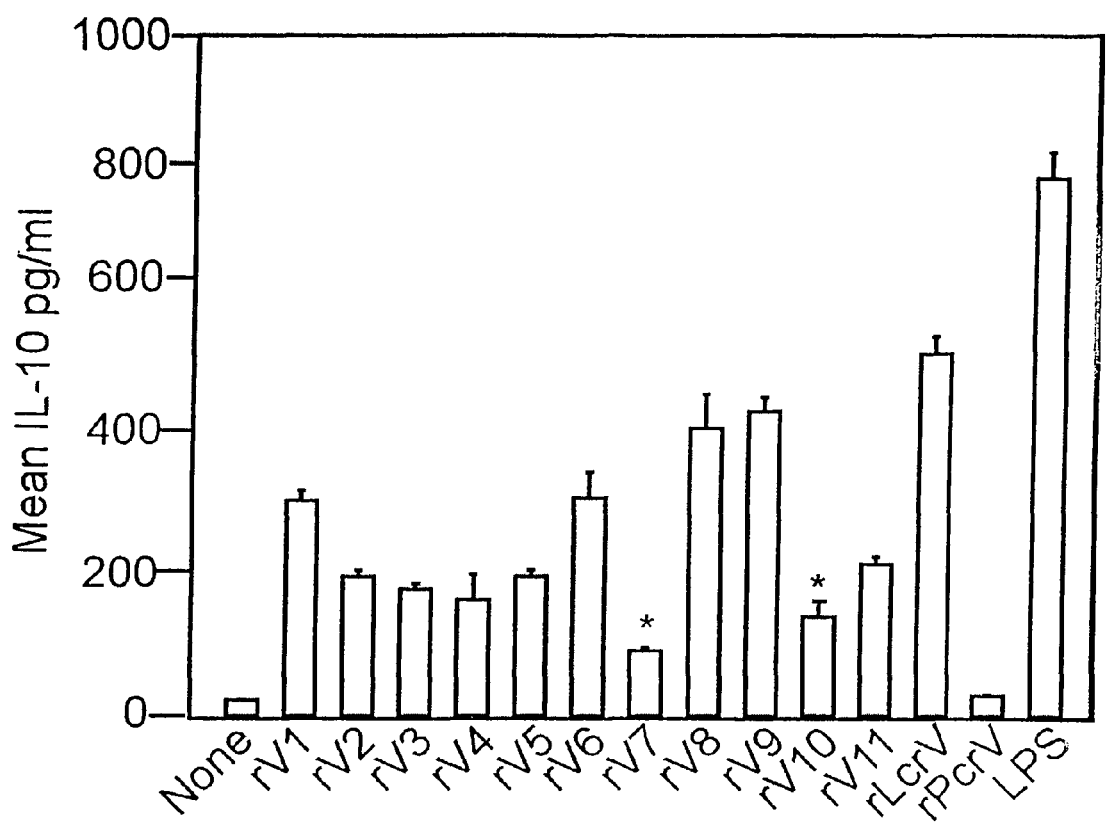
FIG. 4. Induction of IL-10 from murine macrophages stimulated with rLcrV and its variants. Murine peritoneal macrophages were incubated with rLcrV and its variants, rPcrV, LPS or PBS and IL-10 levels determined by ELISA after 18 hours of incubation. The t-test was used to assess statistical significance of observed differences between rLcrV and rV7 ($p \leq 0.005$) or rV10 ($p \leq 0.001$).

Recombinant LcrV (rLcrV) with N-terminal decahistidyl tag was purified from bacterial lysates by affinity chromatography on Ni-NTA. FIG. 3 displays a diagram of the variants. The immune modulatory properties of LcrV are thought to result from an interaction of the *Y. pestis* virulence factor with TLR2 and CD14 on the surface of immune cells, in particular murine macrophages (Sing et al., 2002b). To examine the role of primary immune cells during IL-10 release and rLcrV-mediated immune suppression, macrophages were isolated from the peritoneal cavity of C57BL/6 mice. Peritoneal macrophages were treated with 10 μg rLcrV or its variants and cytokine secretion was analyzed after 18 hours in culture (FIG. 4). rLcrV induced a 40-fold increase in the release of IL-10 from peritoneal macrophages as compared to PBS alone, consistent with previous observations (Sing et al., 2002b). As a control, rPcrV, the *Pseudomonas* protective antigen, failed to induce significant amounts of IL-10 release (Sawa et al., 1999). Although many LcrV variants with short deletions displayed modest decreases in IL-10 release, two mutant proteins, rV7 and rV10, were identified that triggered as much as five-fold less IL-10 in the culture medium of macrophages than samples treated with wild-type rLcrV (FIG. 4). Surprisingly, rV9, a variant that did not induce protective immunity (see below), triggered IL-10 secretion by murine macrophages. As a control for maximum activation of cytokine release, addition of LPS to macrophage cultures caused a 70-fold increase in IL-10 secretion. Together these results demonstrate that the addition of purified rLcrV to isolated primary murine immune cells stimulates the release of IL-10, whereas rV7 and rV10 variants lacking LcrV amino acids 181-210 or 271-300 display significant defects in IL-10 secretion.

Figure 5:
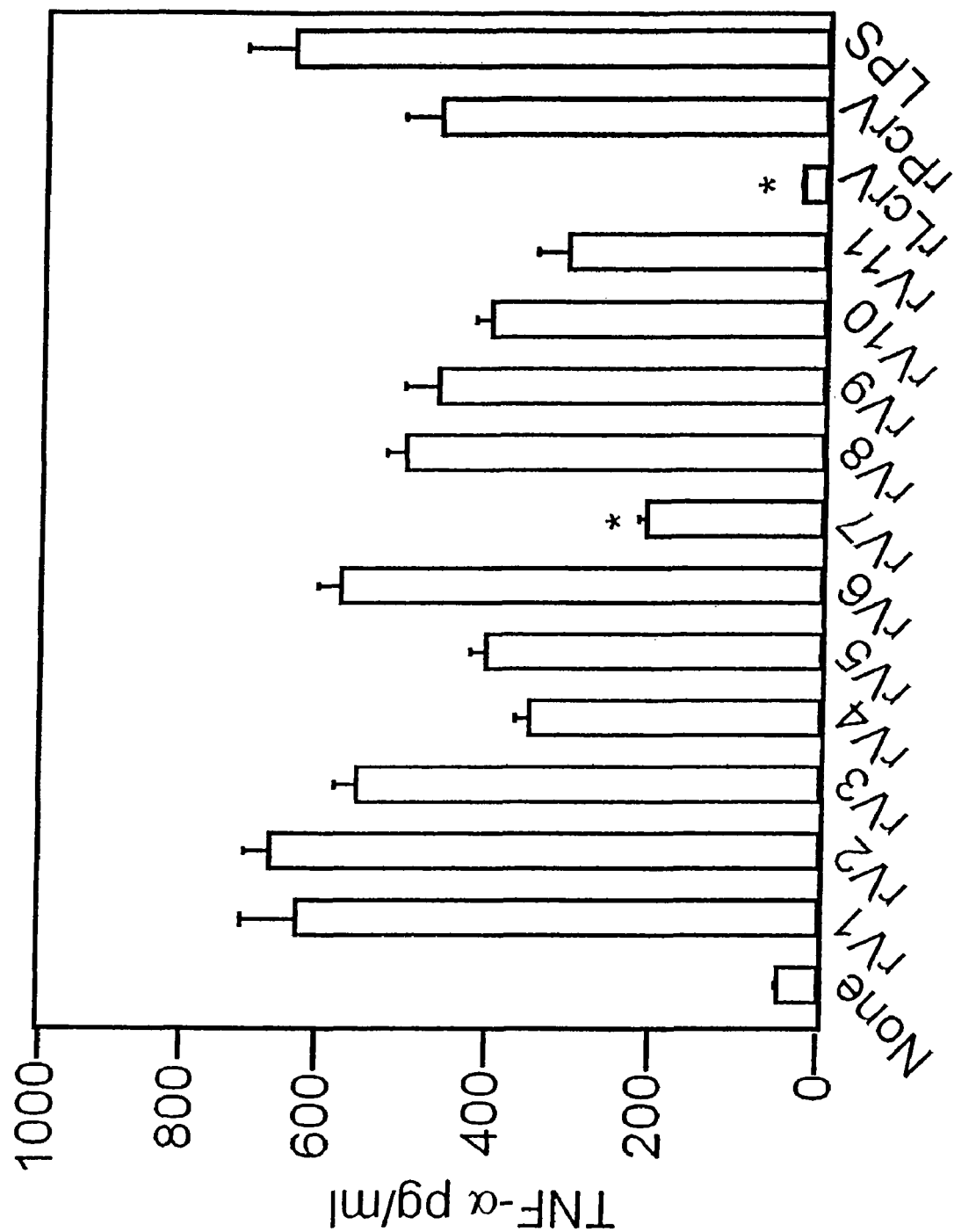
FIG. 5. Immune-modulatory properties of rLcrV and its variants. Murine peritoneal macrophages were treated for two hours with LPS, washed extensively and then treated with rLcrV, its variants or rPcrV. The release of TNF-α after 18 hours was determined by ELISA and compared to that of mock (PBS) stimulated macrophages. The t-test was used to assess statistical significance of observed differences between LPS and rLcrV ($p \geq 0.001$), rV7 ($p \geq 0.02$), rV9 ($p \geq 0.15$) or rV10 ($p \geq 0.05$).

Injection of C57BL/6 mice with LPS or heat killed *Y. pestis*, activates the release of pro-inflammatory cytokines such as IFN-γ and TNF-α (Nakajima et al., 1995). Simultaneous injection of purified rLcrV with LPS or heat killed *Y. pestis* abrogates murine release of IFN-γ and TNF-α in vivo (Nakajima et al., 1995). To test whether rLcrV alone is sufficient to reduce the secretion of pro-inflammatory cytokines from immune cells activated with LPS, we used murine peritoneal macrophages. Treatment of macrophages with LPS led to an expected 35-fold increase in the secretion of TNF-α (FIG. 5). However, if after 2 hours of LPS exposure, macrophages were treated with 10 μg rLcrV, immune cell release of TNF-α was completely blocked (FIG. 5). Addition of rPcrV, rV9 or rV10 caused only a modest reduction in the release of TNF-α from LPS-stimulated macrophages. Together these data suggest that rLcrV has immune-modulatory properties since addition of rLcrV to murine macrophages not only induces IL-10, but also suppresses LPS induced TNF-α production. Of importance for vaccine development, TNF-α suppression was reduced in many rLcrV variants, yet only rV10 lost both the ability to induce IL-10 and the ability to suppress TNF-α production. Surprisingly, rV7, a molecule that failed to activate IL-10 release, triggered a significant reduction in the release of TNF-α from LPS-stimulated macrophages, suggesting that the immune-modulatory functions of rLcrV may involve multiple signaling pathways in murine macrophages.

Example 3 rLcrV Variants and Their Immune Modulatory Properties in Human Cells

Figure 6:
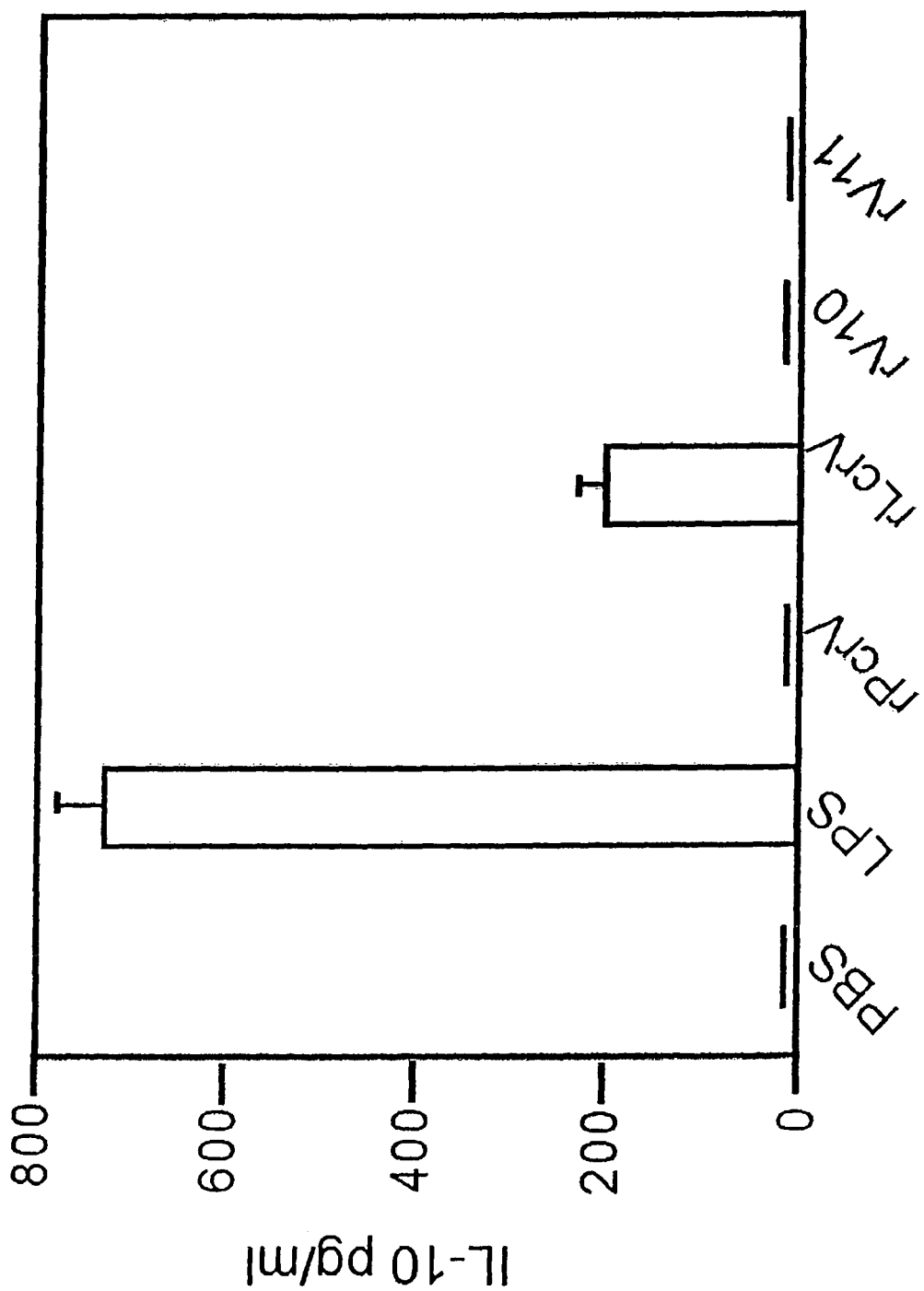
FIG. 6. Induction of IL-10 from human monocytic cells stimulated with rLcrV and its variants. Human THP-1 cells were incubated with rLcrV and its variants, rPcrV, LPS or PBS and IL-10 levels determined by ELISA after 18 hours of incubation. The t-test was used to assess statistical significance of observed differences between rLcrV and rV10 ($p<0.007$) or rV11 ($p<0.006$).

To test whether LcrV activates IL-10 secretion in human cells, purified recombinant proteins were added to human THP-1 monocytic cells and incubated for 18 hours prior to ELISA analysis for cytokines. As a control, addition of LPS to THP-1 cells stimulated IL-10 release 750-fold when compared with PBS mock treated cells. Addition of rLcrV activated IL-10 secretion 180-fold, whereas rPcrV did not stimulate any release of the cytokine. Furthermore, rV10 also failed to activate IL-10 release in human monocytes, similar to our observations in murine macrophages (FIG. 6).

Example 4

Immunization With rV10 Affords Protective Immunity Against Plague

Figures 7A, 7B:
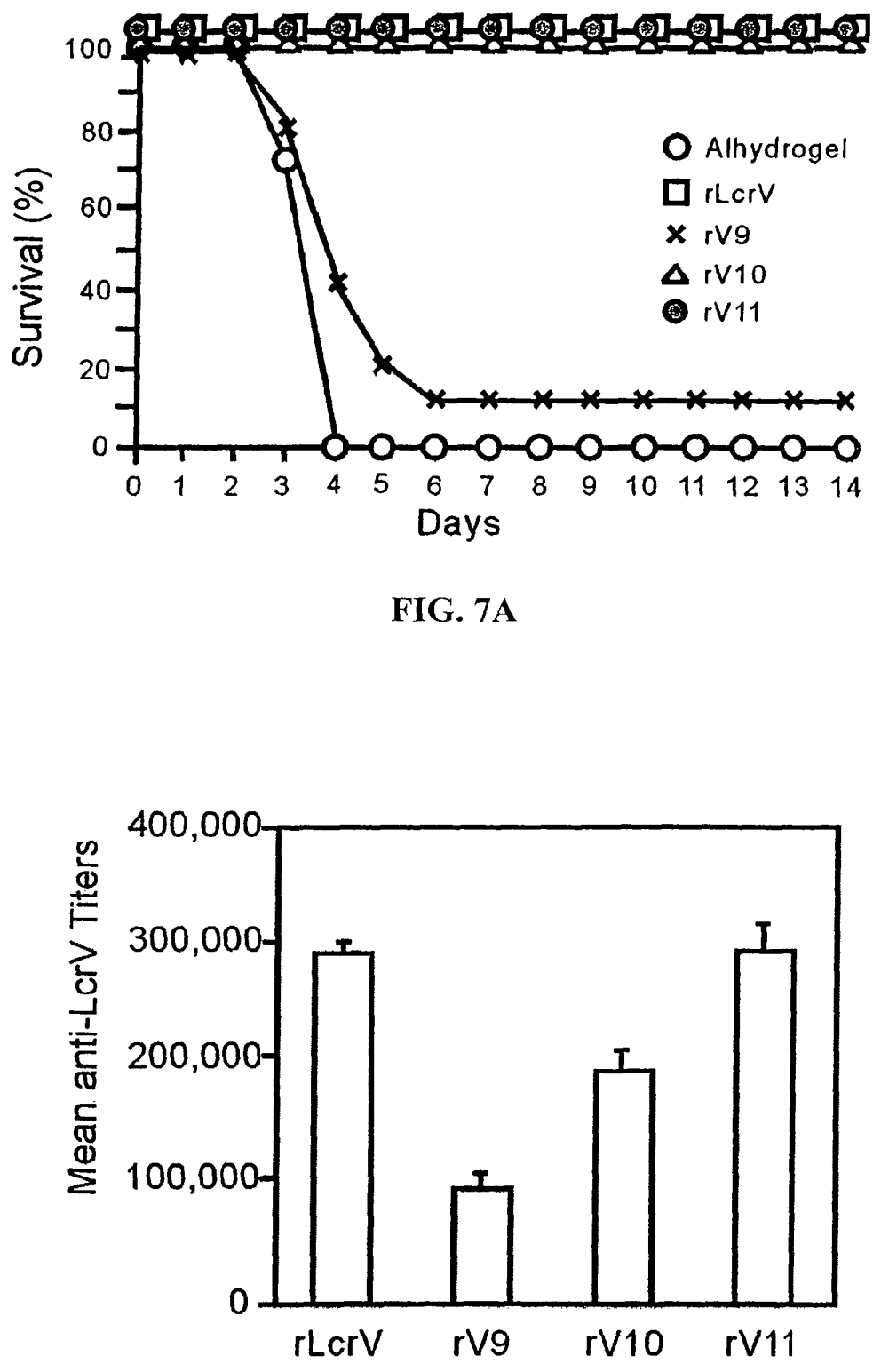

BALB/c mice were immunized with rLcrV or its variants on day 0 and 21 and were challenged with 10 or 1,000 $LD_{50}$ units of *Y. pestis* KIM D27 by intra-venous injection on day 43. As demonstrated previously (Motin et al., 1996), immunization with full length rLcrV completely protected experimental animals against plague at both lethal challenge doses (FIG. 7A and Table 5). Immunization of mice with rV1-5, rV10, and rV11 also completely protected at both lethal challenge doses. The protective antigen property of rV9 was only 10 percent of that observed for rLcrV at the 1,000 $LD_{50}$ challenge dose. Partial protection at 1,000 $LD_{50}$ was observed for rLcrV6, rLcrV7, and rLcrV8, with 80%, 80%, and 90%, survival, respectively. To assess whether vaccine protection occurred after immunization of other mouse strains, C57BL/6 mice were immunized with purified protein on day 0 and 21 and challenged with 1,000 $LD_{50}$ units of *Y.. pestis* KIM D27 by intra-venous injection on day 43. Similar results were obtained for both BALB/c and C57BL/6 mice (Table 5). FIG. 7A shows a time-to-disease analysis of animal infections, documenting the protective immunity afforded by immunization with rLcrV, rV10 and rV 11, whereas rV9 immunization precipitated almost no protection. We sought to assess the ability of recombinant LcrV molecules to elicit a humoral immune response. Mice immunized with rLcrV proteins were bled on day 0, 14, 28 and 42 for analysis of V-antigen specific IgG titers (FIG. 7B and Table 5). Each mouse serum sample was analyzed by ELISA for IgG specific responses. rLcrV variants, in particular rV10 (FIG. 7B), generated similar immune responses as LcrV, indicating that the protective antigen properties of rLcrV had not been significantly impaired by deletion of residues 271-300.

TABLE 5

Immune modulatory and protective antigen properties of LcrV variants

| Antigen[a] | Deleted Residues | Mean IgG[b] | IL-10 (pg/ml)[c] | TNF-α (pg/ml)[c] | 14 day survival 10 $LD_{50}$ | 1,000 $LD_{50}$ |
|---|---|---|---|---|---|---|
| none | NA[f] | NA | 13 | 42 | 0/10[e] | 0/10[d] |
| rLcrV | None | 28,500 | 481 | 34 | 10/10 | 10/10 |
| rV1 | 1-30 | 937,500 | 305 | 609 | 10/10 | 10/10 |
| rV2 | 31-60 | 310,000 | 195 | 391 | 10/10 | 10/10 |
| rV3 | 61-90 | 70,400 | 180 | 360 | 10/10 | 10/10 |
| rV4 | 91-120 | 180,000 | 163 | 325 | 10/10 | 10/10 |
| rV5 | 121-150 | 410,000 | 209 | 417 | 10/10 | 10/10 |
| rV6 | 151-180 | 62,500 | 293 | 587 | 10/10 | 8/10 |
| rV7 | 181-210 | 125,000 | 102 | 204 | 10/10 | 8/10 |
| rV8 | 211-240 | 62,500 | 389 | 779 | 10/10 | 9/10 |
| rV9 | 241-270 | 49,500 | 413 | 825 | 8/9 | 1/10 |
| rV10 | 271-300 | 312,500 | 135 | 271 | 10/10 | 10/10 |
| rV11 | 301-326 | 293,000 | 212 | 424 | 10/10 | 10/10 |
| rPcrV | NA | NA | 26 | 52 | ND | ND |
| LPS | NA | NA | 738 | 1476 | ND | ND |

[a]Purity and identity of antigens was analyzed by Ion Trap Mass Spectrometry.
[b]Mean IgG titers to rLcrV observed 42 days after immunization, immediately before plague challenge.
[c]Observed 15 hours after the addition of rLcrV or its variants to murine primary macrophages.
[d]Challenged with 1,000 $LD_{50}$ (1 × $10^5$ cfu).
[e]Challenged with 10 $LD_{50}$ (1 × $10^3$ cfu).
[f]NA, not applicable; ND, not determined.

Example 5:

Materials and Methods for Examples 6-11

Bacterial Strains and Media

*Yersinia pestis* KIM D27, an attenuated derivative of *Y. pestis* biovar mediaevalis strain KIM lacking the 102-kb pgm locus (Brubaker, 1969), was propagated on Blood Base Agar plates (BB—Difco) at 26 ° C. for two days. Overnight cultures were grown in Heart Infusion Broth (HIA—Difco) at 26° C. Chloramphenicol was added for plasmid selection to a final concentration of 20 µg/ml. *Y. pestis* CO92 is a clinical isolate which is routinely used in experimental models of plague (Davis et al., 1996) and was obtained from Dr. Susan Welkos (United States Army Medical Research Institute of Infectious Disease, Bacteriology Division, Fort Detrick, Md.). *Y. pestis* strain CO92 was propagated on Congo Red agar media (CR—Heart Infusion Agar, 0.2% galactose, 0.01% (w/v) congo red) (Surgalla and Beesley, 1969) for three days at 26 ° C. Overnight cultures were grown in Brain Heart Infusion broth (Difco) at 26 ° C. for 18 hours. Bacterial cells were washed and diluted in PBS. All bacterial suspensions used for infections were diluted and plated on BB (strain KIM D27) or CR (strain CO92) to determine actual inoculation dose. All manipulations with *Y. pestis* CO92 were performed under BSL-3 operating procedures according to institutional guidelines.

Expression and Purification of rLcrV and rV10

*Escherichia coli* BL21 (DE3) (Studier et al., 1990) carrying prLcrV or prV10 (Overheim et al., 2005) was grown overnight at 37° C. in Luria-Bertani medium (LB—Difco) with 100 µg/ml ampicillin. Bacteria were diluted in fresh medium and grown to an $OD_{600}$ of 0.8-1.0. T7 polymerase expression was induced with 1 mM isopropyl-1-thiol-D-galactopyranoside and bacterial growth was continued for 3 hours at 37° C. Cells were harvested by centrifugation at 10,000×g for 10 min. Bacterial sediment was suspended in 20 ml of Tris-HCl (pH 7.5)-150 mM NaCl (column buffer) containing 100 µM phenylmethylsulfonyl fluoride and cells were disrupted by two passages through a French pressure cell at 14,000 psi. The lysate was subjected to ultracentrifugation at 40,000 ×g for 30 min, and the soluble fraction was applied to nickel nitrilotriacetic acid (Ni-NTA) column (1 ml bed volume) pre-equilibrated with 10 ml column buffer. The column was washed with 10 ml of the same buffer, followed by a second (10 ml column buffer with 10% glycerol), and a third washing (10 ml column buffer with 10% glycerol and 20 mM imidazole). Bound protein was eluted in 50 mM Tris-HCl (pH 7.5)-150 mM NaCl, 10% glycerol containing 250 mM imidazole. Purified proteins were subjected to three sequential Triton X-114 (Sigma) phase separations to remove endotoxins (Aida and Pabst, 1990). Purified proteins were applied to a G-25 (Amersham) gel filtration column to remove residual Triton X-114 and then retrieved by phosphate-buffered saline (PBS) elution. Lipopolysaccharide (LPS) contamination of purfied proteins was assayed with Limulus amebocyte lysate (QCL-1000, Cambrex, N.J.) and determined to be less than 1 ng/100µg purified protein. Protein concentrations were determined by the bicinchoninic acid assay (Pierce Technology, Rockford, Ill.). Proteins were aliquoted at 1 mg/ml and stored at -80 ° C. for further use.

Immunization of Mice

Mice were immunized by intra-muscular injection into the hind leg with 50 µg of rLcrV or rV10 emulsified in ALHYDROGEL™ (Sigma), or ALHYDROGEL™ alone as a control. After 21 days, mice were boosted with the same protein/adjuvant formulation. Serum samples were obtained via bleeding from the peri-orbital plexus on day 0and days 14, 28, and 42 following primary immunization. Following blood clotting, sera were retrieved from the supernatants, centrifuged at 1,000×g, and used for measurements of antibody production.

IgG Titer

*Y. pestis* antigen-specific IgG responses in immunized mice were measured by ELISA using individual mouse sera from each animal group. ELISA plates were coated with 100 µl of the purified recombinant antigens at 1 µg/ml and incubated overnight at 4° C. Serially diluted mouse sera (100 µl) were added to each well and assayed in triplicate after blocking. The plates were incubated with horseradish peroxidae-conjugated anti-mouse IgG diluted at 1:10, 000 (100 µl per well), followed by washing and finally developed with 3,3', 5,5'-tetramethybenzidine solution (100 µl per well). The reactions were stopped by adding 25 µl of 2 M $H_2SO_4$, and the plates were read at $OD_{450}$. IgG1 or IgG2a or IgG2B isotype-specific ELISA was conducted as described above, using horseradish peroxidase (HRP)-conjugated goat-anti-mouse IgG1 or IgG$_2$a or IgG2B (Jackson Immunoresearch, Pa.) at 1:1000, 1:500 or 1:500 dilution, respectively. Specific IgG titers were estimated as the maximum dilution of serum generating absorbance at 450 nm of 0.1 units over background. Using this antibody titer, mean antibody titers± standard error of mean (SEM) were derived per immunization group.

β-Lactamase Assay In Vaccinated Mice 6-8 week old female C57BL/6 mice were obtained from The Jackson Laboratory (Bar Harbor, Me.). Groups of 7 mice were immunized as described above. On day 43, mice were challenged with *Y. pestis* KIM D27 carrying either pMM83 (YopM-Bla) or pMM91 (Gst-Bla) as previously described (Marketon et al., 2005). Briefly, overnight cultures were diluted 1:20 into fresh HIB containing chloramphenicol and grown for 3 hours at 26 ° C. Cultures were washed and diluted to $10^4$ CFU/ml in PBS. Mice were anesthetized with 100-130 mg/kg ketamine and 3-6 mg/kg xylazine and infected via injection into the retro-orbital plexus with $10^3$ CFU. On day 2 post infection, 3 mice per vaccination set were euthanized and spleens were harvested. Splenocytes were stained with 0.125×CCF2-AM for flow cytometry analysis as previously described (Marketon et al., 2005).

T Cell Proliferation Assay

BALB/c mice were immunized subcutaneously with 100 μg rLcrV, rV10, or rPcrV emulsified in ALHYDROGEL™ (Sigma) at three sites on the rear flank. On day 8following immunization, mice were euthanized and draining lymph nodes were harvested. Single cell suspensions of draining lymph nodes were prepared by mechanical disruption through nylon mesh. The cell suspension was depleted of non-T cells by magnetic sorting. Briefly, cells were incubated at 10$^7$ cells/ml with Pan-T cell Microbeads (Miltenyi Biotec, Auburn, CA). After 20 min of rotation at 4° C., single cell suspensions were depleted of non-T cells by separation in a Miltenyi AutoMacs machine. Syngeneic splenocytes used as antigen presenting cells were irradiated at 3,000 rads and suspended at $4\times10^6$ cells/ml. T cells were cultured with the irradiated splenocytes at a ratio of 4:1 (T cell to APC) in 10% fetal calf serum in RPMI-1640with 100 U/ml penicillin (Life Technologies), 100 μg/ml streptomycin (Life Technologies), $5\times10^{-5}$ M 2-mercaptoethanol in the presence of 0, 0.1, 1, 10 μg/ml rLcrV, rV10, rPcrV or ovalbumin (Sigma) in 96 flat bottomed well plates. Cells were incubated at 37 ° C. in a humidified atmosphere containing 7.5% $CO_2$. The cells were pulsed with 1 μCi [$^3$H]TdR (ICN Radiochemicals, Irvine, CA) after 72 hours, harvested after 96 hours and [$^3$H]TdR uptake was detected using a Packard Topcount microplate scintillation counter (Packard Instruments). Results are presented as the mean ± SEM of triplicate wells.

Subcutaneous challenge with *Y. pestis* CO92. 6-8 week old female BALB/c mice were obtained from Charles River Laboratories (Wilmington, MA). Groups of 10 mice were immunized as described above. On day 43, mice were challenged with *Y. pestis* CO92 by subcutaneous injection into the hind flank. Animals were returned to their cages and monitored for signs of acute infection. Animals that exhibited signs of terminal illness were euthanized by $CO_2$ asphyxiation. All animals infected with *Y. pestis* strain CO92, whether they exhibit signs of acute infection or not, were euthanized 14 days post infection.

Intranasal challenge with *Y. pestis* CO92. 6-8 week old female BALB/c mice were obtained from Charles River Laboratories (Wilmington, Mass.). Groups of 10 mice were immunized as described above. On day 43, mice were challenged with *Y. pestis* CO92 by intranasal inoculation. For this procedure, animal were anesthetized with 100-130 mg/kg ketamine and 3-6 mg/kg xylazine. Bacterial suspensions were pipetted into the nares, mice were returned to their cages and monitored for signs of acute infection. For each bacterial dose, 1 mouse was euthanized 30-60 minutes after inoculation, and lungs were removed, homogenized in PBS, and plated on CR to determine actual deposition of bacteria in the lungs. Animals exhibiting signs of terminal illness were euthanized by $CO_2$ asphyxiation and lungs and spleens were harvested. Samples were homogenized in PBS, diluted, and plated on CR plates to determine bacterial load in the tissues.

All animal experiments were performed in accordance with institutional guidelines following experimental protocol review and approval by the Institutional Biosafety Committee and the Institutional Animal Care and Use Committee. The 50% acute disease dose was determined using the Reed Muench formula (Reed and Muench, 1938).

Example 6 rV10 Protects Against Bubonic Plague

Previous work determined the $LD_{50}$ of *Y. pestis* CO92 to be approximately 1-2 CFU via the subcutaneous route of infection (Example 4, Welkos et al., 1997). A similar $LD_{50}$ value was measured for *Y. pestis* CO92 in a subcutaneous infection model in BALB/c mice (data not shown). To determine whether rLcrV and rV10 provided similar levels of protection against bubonic plague, purified recombinant rLcrV and rV10 vaccine antigens were emulsified with ALHYDROGEL™. Groups of 10 BALB/c mice were immunized with adjuvant alone, or 50 μg LcrV or rV10 on day 0 followed by a booster with an equal dose on day 21. Blood from 5 mice in each immunization set was taken on days 0, 14, 28, and 42 after primary immunization to measure the generation of specific antibodies. On day 43, mice were challenged with 100,000 lethal doses of *Y. pestis* CO92 via subcutaneous injection. Immunization with either rLcrV or rV10 protected all mice in this study against lethal challenge, whereas mice receiving adjuvant alone succumbed to disease within four days after infection with a mean time to death of 2 .5 days (FIG. 9). These data demonstrate that rV10 provides robust protection against bubonic plague infections, similar to rLcrV.

Example 7

Pneumonic Plague Model in BALB/c Mice

Pneumonic plague infections in mice can be precipitated via aerosol inhalation or intranasal infection. Aerosol infection of mice is technically demanding and requires very high doses of *Y. pestis*, consistent with the notion that aerosolization procedures damage plague bacteria (Anderson et al., 1996). The pneumonic plague model in BALB/c mice is not firmly established in the literature, particularly when animals are infected with *Y. pestis* through intranasal inoculation (Wang et al., 2004). In order to test rV10 for efficacy against pneumonic plague, we developed an intranasal infection model of *Y. pestis* CO92 in BALB/c mice. Groups of 10 mice were infected with bacterial suspension delivered by the intranasal route. Actual deposition in the lungs was determined by postmortem removal of lungs 60 minutes after inoculation, followed by plating of tissue homogenate and colony formation. It was observed that 60 minutes after infection with $1.9\times10^5$ CFU *Y. pestis* CO92, greater than 80% of inoculated Yersiniae were found deposited in lung tissues.

Animals were monitored for 14 days for signs of acute disease and time to death recorded (FIG. 10A). An average dose of 389 CFU (MLD) caused acute lethal disease in half of all experimental animals, consistent with previous observations of Goguen and colleagues using *Y. pestis* strain KIM and intranasal infection of mice (Wang et al., 2004). The average time to death varied, depending on dose, with high dose animals succumbing to infection on day 2, while animals infected with lower doses developed lethal infections 4 days after inoculation. To examine bacterial dissemination after intranasal infection, animals that exhibited signs of terminal illness were euthanized by $CO_2$ asphyxiation and bacterial load in lungs and spleens determined by plating tissue homogenate on CR agar (FIG. 10B). Mice infected with high doses, $1.9 \times 10^5$ and $2.4 \times 10^3$ CFU, were euthanized on day 2, while mice from the low dose (430 CFU) were euthanized on day 4, when animals showed signs of terminal illness. All three doses produced acute plague disease in mice with high bacterial titers in lungs and spleen (FIG. 10B) as well as blood. Bacteria recovered from host tissues retained the pigmentation phenotype as evidenced by the formation of red colonies on CR plates. Together these data suggest that intranasally infected mice developed systemic plague infections.

Example 8 rV10 Protects against Pneumonic Plague

The intranasal infection model for pneumonic plague in mice was used to compare vaccine efficacies between rLcrV and rV10. Groups of 10 BALB/c mice were immunized following the two dose regimen described above. On day 43 after primary immunization, mice were challenged with 2,570 MLD of *Y. pestis* CO92 (1,000,000 CFU) by intranasal inoculation. Surprisingly, rLcrV only provided 70% protection in this experiment, whereas mice immunized with rV10 were completely protected (FIG. 11). These data suggest that rV10 vaccination is at least as efficacious against lethal pneumonic plague challenge as rLcrV immunization. Sera collected from immunized mice on day 42 after primary immunization were analyzed for total IgG specific for LcrV or rV10 by modified ELISA. Results were normalized against the reactivity measured in mice vaccinated with ALHYDROGEL™alone (Table 6). These data showed on average a 4 fold increase in anti-rLcrV IgG antibody titer in rV10vaccinated mice when compared with rLcrV vaccinated mice. To determine whether humoral immune responses to vaccination differed between mouse strains, 10 animals each of mouse strains BALB/c and C57/BL6 were immunized with rLcrV or rV10 and antigen specific IgG titers were determined (Table 6). rV10immunization elicited 5.2 (BALB/c) and 3.32 (C57/BL6) fold higher titers of antigen specific IgG than rLcrV immunization.

TABLE 6

IgG Titers elicited by rV10 and rLcrV immunization

| Antigen | BALB/c | C57/BL6 |
|---|---|---|
| rLcrV | $2.5 \times 10^4$ | $2.5 \times 10^4$ |
| rV10 | $1.3 \times 10^5$ | $8.4 \times 10^4$ |

Animals were immunized by intramuscular injection with 50 μg purified antigen emulsified with ALHYDROGEL ™ into the hind leg on day 0 and 21. Serum samples on day 43 were analyzed for anti-LcrV specific IgG titers.

Example 9 rV10 Provides Improved Protection Against Pneumonic Plague

To further characterize the efficacy of rV10 and rLcrV in mice, breakthrough challenges in protection afforded by the two vaccines were investigated. Towards this end, mice were vaccinated with adjuvant, rLcrV or rV10 following the regimen described above. On day 43 after immunization, mice were infected with bacterial doses ranging from $4.5\times10^5$ to $4.0\times10^8$ CFU. Two mice from each dose group were euthanized 60 min following infection to determine bacterial deposition in the lung by plating on HIA and CR agar. Mice were then monitored for 14 days for signs of acute disease and time to disease recorded. All adjuvant control mice succumbed to disease with a mean time to death of 2.1 days (Table 7). In contrast, mice vaccinated with rLcrV or rV10 were fully protected at a challenge dose of $4.5\times10^5$ CFU. Mice immunized with rV10 and challenged with $6.7\times10^6$ or $5.6\times10^7$ CFU were also fully protected (Table 7). The latter dose corresponds to 144,000 MLD for the pneumonic plague model. In contrast, mice immunized with rLcrV were only partially protected as 1/9 and 2/9 animals, respectively, succumbed to infection. The mean time to death for these mice was 3 days. At the highest dose of infection, $4.0\times10^8$ CFU corresponding to 1,000,000 MLD, rV10 offered partial protection as 6/9 mice succumbed to infection. rV10 vaccinated mice displayed delayed time to acute disease, with a mean time to death of 4.2 days. rLcrV vaccination protected only 2/9 mice and mice that succumbed to infection did so with a mean time to death of only 2.4 days. These data suggest that, in comparison with rLcrV, rV10 vaccination offers at least equal, if not greater levels of protection in the murine pneumonic plague model (Table 7).

TABLE 7

Vaccine protection elicited by rV10 and rLvrV immunization against intranasal challenge with *Y. pestis* CO92

| Inoculum (CFU) | ALHYDROGEL ™ | rLcrV | rV10 |
|---|---|---|---|
| $4.5 \times 10^5$ | 0/9 (2.1) | 9/9 | 9/9 |
| $6.7 \times 10^6$ | NT | 8/9 (3.0) | 9/9 |
| $5.6 \times 10^7$ | NT | 7/9 (3.0) | 9/9 |
| $4.0 \times 10^8$ | NT | 2/9 (2.4) | 3/9 (4.2) |

Anesthetized animals were infected by intranasal inoculation and observed for 14 days for the development of plague. Numbers indicate surviving animals/total experimental cohort. Numbers in parenthesis indicate the mean time of survival (in days).

Example 10 rV10 Vaccination Provides for Improved Clearance of *Y. pestis* KIMD27

Whether vaccination with rV10 provided improved clearance of *Y. pestis* during infections was investigated. Towards this end, a recently developed assay to measure type III injection during infection was employed (Marketon et al., 2005). In this assay, β-lactamase lactamase is fused to YopM, an effector protein that is delivered by *Y. pestis* into host cells via the type III injection pathway (Marketon et al., 2005). *Y. pestis* KIM D27 expressing YopM-Bla is then used to infect C57/BL6 mice. Injection of this reporter protein into host leukocytes is detected with the use of CCF2-AM, a fluorescent substrate for β-lactamase (Marketon et al., 2005). CCF2-AM is a membrane-permeant ester with two fluorophores attached to cephalosporin that exhibit fluorescence resonance energy transfer (FRET). Excitation of coumarin (409 nm) results in green fluorescence emission from fluorescein (520 mn) in intact CCF2-AM. When the YopM reporter is injected into host cells, β-lactamase cleaves CCF2-AM, thereby disrupting FRET and establishing blue fluorescence emission which can be measured by flow cytometry.

Groups of seven C57/BL6 mice were immunized with adjuvant alone, LcrV or rV10 following the 2 dose regimen described above. On day 43, mice were infected intravenously with 1,000 CFU of $Y.$ $pestis$ KIM D27 carrying either YopM-Bla or GST-Bla, a control hybrid that cannot travel the type m pathway (Marketon et al., 2005). This infection dose corresponds to approximately 10 $LD_{50}$ in this model (Overheim et al., 2005). On day 2 post-infection, mice were euthanized and spleens harvested. For each mouse, the spleen was homogenized and an aliquot plated in triplicate on HIA supplemented with chloramphenicol to select for the presence of the reporter plasmid for bacterial enumeration. The remaining sample was treated with CCF2-AM and subjected to flow cytometry to permit quantification of injection of YopM-Bla into splenocytes (FIG. 12A-C). All mice that received adjuvant developed high bacterial titers in the spleen, ranging from $10^6$ to $10^7$ CFU (FIG. 12A). In contrast, one of the mice that had been immunized with LcrV developed colonization of the spleen, though no disease symptoms were apparent in this animal. Moreover, all mice that had been immunized with rV10 had no detectable bacteria in the spleen. When analyzed by flow cytometry, mice immunized with adjuvant alone and infected with $Y.$ $pestis$ expressing YopM-Bla harbored a significant proportion of blue cells, as 1.77% of all live splenocytes were injected with the fusion protein. As expected from earlier results, adjuvant mice infected with GST-Bla $Yersinia$ harbored no blue cells (FIG. 12B). One mouse that had been first vaccinated with LcrV and then infected with $Y.$ $pestis$ expressing YopM-Bla, harbored 1% blue splenocytes, consistent with the presence of $Y.$ $pestis$ colony forming units in the spleen. No blue cells could be found in the other two mice in this set for which no bacteria were recovered in the spleen. These data suggest rLcrV vaccination provided partial clearance of $Y.$ $pestis$, presumably by either reducing type III injection of immune cells or by promoting phagocytosis of the bacteria. In contrast, as none of the rV10 vaccinated mice that were infected with $Y.$ $pestis$ expressing YopM-Bla harbored blue cells and no bacteria were recovered from the spleens of these animals, it appears that rV10 vaccination efficiently clears the bacteria. It should be noted that this assay does not permit distinction between a block in type III injection or an increase in phagocytosis that may be caused by the rV10/rLcrV specific antibodies. Recently, other investigators have shown that LcrV vaccination results in the production of antibodies that provide protection against plague by either improving the efficiency with which the bacteria are phagocytosed by host polymorphonuclear cells (PMNs) or by blocking type m injection of effector proteins (44, 62). Regardless of the mechanism, these data suggest that antibodies to rV10 and rLcrV neutralize infections by similar molecular mechanisms.

Example 11

Humoral and Cellular Immunogenicity of rV10

Immune sera from BALB/c mice vaccinated with either rLcrV or rV10 were further characterized for the immunoglobulin isotype profile by ELISA. Animals receiving either one of these two vaccines responded with the predominant production of IgG1 type antibodies, indicative of a Th1 type immune response (FIG. 13). Mice immunized with rLcrV showed little to no IgG2a and IgG2b isotypes, consistent with previously reported observations (Jones et al., 2001). Vaccination with rV10 allowed the development of a humoral immune response which appears to be increased when compared with that of rLcrV, as serum IgG1, 2a and 2b isotypes titers were observed in all vaccinated animals (FIG. 13). These data suggest that vaccination with rV10 elicits a strong Th1 response, but may also stimulate the Th2 pathway, as IgG2a antibodies are indicative of a Th2 response.

Figure 14:
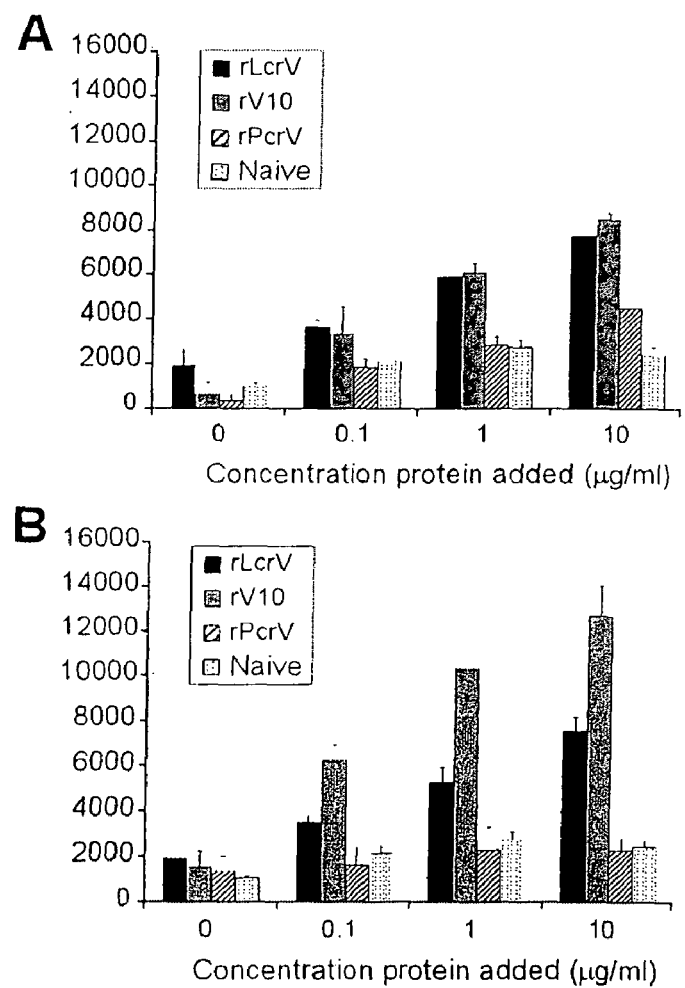

To further characterize the T-cell response to rV10 vaccination, rLcrV and rV10 were assayed for the ability to stimulate primary T cells. As a measure of T cell reactivity, we performed a T cell proliferation assay on splenic cells isolated from vaccinated mice in response to stimulation by homologous or heterologous antigen. For this experiment, an analysis of rPcrV was included because it is a homolog of LcrV in $Pseudomonas$ $aeruginosa$ which is known to induce a protective immune response without concomitant induction of anti-inflammatory cytokines (40, 51). Briefly, BALB/c mice were immunized subcutaneously with rLcrV, rV10, or rPcrV. On day 8 following immunization, T cells were purified from the draining lymph nodes by magnetic bead sorting. T cells were cultured with irradiated antigen presenting cells in the presence of rLcrV, rV10 or rPcrV, pulsed with 1 μCi [$^3$H]TdR after 72 hours of culture and were then harvested at 96 hours. Cellular uptake of [$^3$H]TdR is shown in FIG. 14. T cells from mice immunized with rLcrV or rV10 followed by stimulation with the same antigen responded by proliferating approximately 4 fold, suggestive of a T cell response following vaccination with rLcrV or rV10 (FIG. 14A). In contrast, rPcrV showed only a minor proliferative response. Interestingly, mice immunized with rV10 followed by stimulation with wild-type rLcrV, a situation that more closely mimics the in vivo model of immunization followed by challenge, responded with more than six-fold proliferation (FIG. 14B). Together these results suggest that rLcrV immunization elicits a T cell response, however rV10 booster immunization appears to produce higher T cell responses than rLcrV immunizations.

All of the compositions and methods disclosed and claimed herein can be made and executed without undue experimentation in light of the present disclosure. While the compositions and methods of this invention have been described in terms of embodiments of the invention, it will be apparent to those of skill in the art that variations may be applied to the compositions and methods and in the steps or in the sequence of steps of the method described herein without departing from the concept, spirit and scope of the invention. More specifically, it will be apparent that certain agents, which are both chemically and physiologically related, may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references are specifically incorporated herein by reference.

U.S. Pat. No. 3,791,932
U.S. Pat. No. 3,949,064
U.S. Pat. No. 4,174,384
U.S. Pat. No. 4,367,110
U.S. Pat. No. 4,452,901
U.S. Pat. No. 4,554,101

U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,683,195
U.S. Pat. No. 4,683,202
U.S. Pat. No. 4,683,202
U.S. Pat. No. 4,684,611
U.S. Pat. No. 4,690,915
U.S. Pat. No. 4,800,159
U.S. Pat. No. 4,952,500
U.S. Pat. No. 5,028,592
U.S. Pat. No. 5,084,269
U.S. Pat. No. 5,199,942
U.S. Pat. No. 5,221,605
U.S. Pat. No. 5,238,808
U.S. Pat. No. 5,302,523
U.S. Pat. No. 5,310,687
U.S. Pat. No. 5,322,783
U.S. Pat. No. 5,384,253
U.S. Pat. No. 5,464,765
U.S. Pat. No. 5,538,877
U.S. Pat. No. 5,538,880
U.S. Pat. No. 5,550,318
U.S. Pat. No. 5,563,055
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,620,896
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,843,650
U.S. Pat. No. 5,846,709
U.S. Pat. No. 5,846,783
U.S. Pat. No. 5,849,497
U.S. Pat. No. 5,849,546
U.S. Pat. No. 5,849,547
U.S. Pat. No. 5,858,652
U.S. Pat. No. 5,866,366
U.S. Pat. No. 5,871,986
U.S. Pat. No. 5,916,776
U.S. Pat. No. 5,922,574
U.S. Pat. No. 5,925,565
U.S. Pat. No. 5,928,905
U.S. Pat. No. 5,928,906
U.S. Pat. No. 5,928,906
U.S. Pat. No. 5,932,451
U.S. Pat. No. 5,935,819
U.S. Pat. No. 5,935,825
U.S. Pat. No. 5,939,291
U.S. Pat. No. 5,942,391
U.S. Pat. No. 5,945,100
U.S. Pat. No. 5,958,895
U.S. Pat. No. 5,981,274
U.S. Pat. No. 5,994,624
U.S. Pat. No. 6,651,655
U.S. Pat. No. 6,656,462
U.S. Pat. No. 6,733,754
U.S. Pat. No. 6,793,923
U.S. Pat. No. 6,814,971

U.S. Pat. No. 6,821,957
Aida and Pabst, *J. Immunol. Methods*, 132:191-195, 1990.
Anderson et al., *Infect. Immun.*, 64:4580-4585, 1996.
Angel et al., *Mol. Cell. Biol.*, 7:2256, 1987.
Angel et al., *Cell*, 49:729, 1987b.
Angel et al., *Mol. Cell. Biol.*, 7:2256, 1987a.
Anisimov, et al, *Clin. Microbiol. Rev.*, 17(2):434-464, 2004.
Atchison and Perry, *Cell*, 46:253, 1986.
Atchison and Perry, *Cell*, 48:121, 1987.
Ausubel et al., In: *Current Protocols in Molecular Biology*, John, Wiley & Sons, Inc, New York, 1996.
Banerji et al., *Cell*, 27(2Pt 1):299-308, 1981.
Banerji et al., *Cell*, 33(3):729-740, 1983.
Barany and Merrifield, In: *The Peptides, Gross and Meienhofer* (Eds.), Academic Press, NY, 1-284, 1979.
Bartelloni et al., *Mill. Med.*, 138:720-722, 1973.
Bellus, *J. Macromol. Sci. Pure Appl. Chem.*, A31(1): 1355-1376, 1994.
Bergmann et al., *J. Bacteriol.*, 173:1607-1616, 1991.
Berkhout et al., *Cell*, 59:273-282, 1989.
Blanaretal., *EMBO J.*, 8:1139, 1989.
Bodine and Ley, *EMBO J.*, 6:2997, 198.
Boisier et al., *Emerg. Infect. Dis.*, 8:311-316, 2002.
Boshart et al., *Cell*, 41:521, 1985.
Bosze et al., *EMBO J.*, 5(7):1615-1623, 1986.
Braddock et al., *Cell*, 58:269, 1989.
Brubaker, *Infect. Immun.*, 3673-3681, 2003.
Brubaker, *J. Bacteriol.*, 98:1404-1406, 1969.
Brutlag et al., *Comput. Appl. Biosci.*, 6(3):237-245, 1990.
Bulla and Siddiqui, *J. Virol.*, 62:1437, 1986.
Burrows, Ergebn. *Mikrobiol.*, 37:59-113, 1963.
Burrows, *Nature*, 177:426-427, 1956.
Burrows, *Nature*, 179:1246-1247, 1957.
Butler, In: *Piague and other Yersinia infections*, Plenum Press, NY, 1983.
Campbell and Villarreal, *Mol. Cell. Biol.*, 8:1993, 1988.
Campere and Tilghman, *Genes and Dev.*, 3:537, 1989.
Campo et al., *Nature* 303:77, 1983.
Carbonelli et al., *FEMS Microbiol. Lett.*, 177(1):75-82, 1999.
Celander and Haseltiyne, *J. Virology*, 61:269, 1987.
Celander et al., *J. Virology*, 62:1314, 1988.
Chandler et al., *Cell*, 33:489, 1983.
Chandler et al., *Proc. Natl. Acad. Sci. USA*, 94(8):3596-601, 1997.
Chang et al., *Mol. Cell. Biol.*, 9:2153, 1989.
Chatterjee et al., *Proc. Natl. Acad. Sci. USA*, 86:9114, 1989.
Chen and Okayama, *Mol. Cell Biol.*, 7(8):2745-2752, 1987.
Choi et al., *Cell*, 53:519, 1988.
Chou and Fasman, *Adv. Enzymol.*, 47:45-148, 1978a.
Chou and Fasman, *Annu. Rev. Biochem.*, 47:251-276, 1978b.
Chou and Fasman, *Biochemistry*, 13(2):211-222, 1974a.
Chou and Fasman, *Biochemistry*, 13(2):222-245, 1974b.
Chou and Fasman, *Biophys. J.*, 26(3):385-399, 1979.
Cocea, *Biotechniques*, 23(5):814-816, 1997.
Cohen et al., *J. Cell. Physiol.*, 5:75, 1987.
Costa et al., *Mol. Cell. Biol.*, 8:81, 1988.
Craven et al., *J. Med. Entomol.*. 30:758-761, 1993.
Cripe et al, *EMBO J.*, 6:3745, 1987.
Culotta and Hamer, *Mol. Cell. Biol.*, 9:1376, 1989.
Dandolo et al., *J. Virology*, 47:55-64, 1983.
Davis et al., *Arch. Pathol. Lab. Med.*, 120:156-163, 1996.
Davis et al., *Science*, 304:736-738, 2004.
De Villiers et al., *Nature* 312(5991):242-246, 1984.
Derewenda et al., *Structure*, 12:301-306, 2004.
Deschamps et al., *Science*, 230:1174-1177, 1985.
Edbrooke et al., *Mol. Cell. Biol.*, 9:1908, 1989.
Edlund et al., *Science*, 230:912-916, 1985.

Fechheimer, et al., *Proc. Natl. Acad. Sci. USA*, 84:8463-8467, 1987.
Feng and Holland, *Nature* 334:6178, 1988.
Fetrow and Bryant, *Biotechnology* (NY), 1 1(4):479-484, 1993.
Firak and Subramanian, *Mol. Cell. Biol.*, 6:3667, 1986.
Foecking and Hofstetter, *Gene*, 45(1):101-105, 1986.
Fraley et al., *Proc. Natl. Acad. Sci. USA*, 76:3348-3352, 1979.
Freshney, In: *Animal Cell Culture*, A Practical Approach, 2$^{nd}$ Ed., Oxford Press, UK, 1992.
Fujita et al., *Cell*, 49:357, 1987.
GB Appln. 2 202 328
Gilles et al., *Cell*, 33:717, 1983.
Gloss et al., *EMBO J.*, 6:3735, 1987.
Godbout et al., *Mol. Cell. Biol.*, 8:1169, 1988.
Goodboum and Maniatis, *Proc. Natl. Acad. Sci. USA*, 85:1447, 1988.
Goodboum et al., *Cell*, 45:601, 1986.
Gopal, *Mol. Cell Biol.*, 5:1188-1190, 1985.
Graham and Van Der Eb, *Virology*, 52:456-467, 1973.
Greene et al., *Immunology Today*, 10:272, 1989
Grosschedl and Baltimore, *Cell*, 41:885, 1985.
Guex and Peitsch, *Electrophoresis*, 18:2714-2723, 1997.
Harland and Weintraub, *J. Cell Biol.*, 101(3):1094-1099, 1985.
Haslinger and Karin, *Proc. Natl. Acad. Sci. USA*, 82:8572, 1985.
Hauber and Cullen, *J. Virology*, 62:673, 1988.
Heath et al., *Vaccine*, 16:1131-1137, 1998.
Hen et al., *Nature* 321:249, 1986.
Hensel et al., *Lymphokine Res.*, 8:347, 1989.
Herr and Clarke, *Cell*, 45:461, 1986.
Hill et al., *Infect. Immun.*, 65:4476-4482, 1997.
Hirochika et al., *J. Virol.*, 61:2599, 1987.
Hirsch et al., *Mol. Cell. Biol.*, 10:1959, 1990.
Holbrook et al., *Virology*, 157:211, 1987.
Horlick and Benfield, *Mol. Cell. Biol.*, 9:2396, 1989.
Huang et al., *Cell*, 27:245, 1981.
Hug et al., *Mol. Cell. Biol.*, 8:3065, 1988.
Hwang et al., *Mol. Cell. Biol.*, 10:585, 1990.
Imagawa et al., *Cell*, 51:251, 1987.
Imbra and Karin, *Nature* 323:555, 1986.
Imler et al., *Mol. Cell. Biol.*, 7:2558, 1987.
Imperiale and Nevins, *Mol. Cell. Biol.*, 4:875, 1984.
Inglesby et al., *JAMA*, 293:2281-2290, 2000.
Innus et al., *Proc. Natl. Acad. Sci. USA*, 85(24):9436-9440, 1988.
Inouye and Inouye, *Nucleic Acids Res.*, 13:3101-3109, 1985.
Jakobovits et al., *Mol. Cell. Biol.*, 8:2555, 1988.
Jameel and Siddiqui, *Mol. Cell. Biol.*, 6:710, 1986.
Jameson and Wolf, *Comput. Appl. Biosci.*, 4(1):181-186, 1998.
Jaynes et al., *Mol. Cell. Biol.*, 8:62, 1988.
Johnson et al., *Mol. Cell. Biol.*, 9:3393, 1989.
Jones et al., *Vaccine*, 19:358-366, 2001.
Kadesch and Berg, *Mol. Cell. Biol.*, 6:2593, 1986.
Kaeppler et al., *Plant Cell Reports*, 9:415-418, 1990.
Kaneda et al., *Science*, 243:375-378, 1989.
Karin et al., *Mol. Cell. Biol.*, 7:606, 1987.
Karin et al., *Mol. Cell. Biol.*, 7:606, 1987.
Katinka et al., *Cell*, 20:393, 1980.
Kato et al, *J. Biol. Chem.*, 266:3361-3364, 1991.
Kawamoto et al., *Mol. Cell. Biol.*, 8:267, 1988.
Kiledjian et al., *Mol. Cell. Biol.*, 8:145, 1988.
Klamut et al., *Mol. Cell. Biol.*, 10:193, 1990.
Koch et al., *Mol. Cell. Biol.*, 9:303, 1989.
Kopp and Medzhitov, *J. Exp. Med.*, 196:1009-1012, 2002.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Kuhl et al., *Cell*, 50:1057, 1987.
Kunz et al., *Nucl. Acids Res.*, 17:1121, 1989.
Kyte and Doolittle, *J. Mol. Biol.*, 157(1):105-132, 1982.
Larsen et al., *Proc. Natl. Acad. Sci. USA*, 83:8283, 1986.
Laspia et al., *Cell*, 59:283, 1989.
Latimer et al., *Mol. Cell. Biol.*, 10:760, 1990.
Leary et al., *Infect. Immun.*, 63:2854-2858, 1995.
Lee et al., *J. Biol. Chem.*, 275:36869-36875, 2000.
Lee et al., *Nature* 294:228, 1981.
Lee et al., *Nucleic Acids Res.*, 12:4191-206, 1984.
Levenson et al., *Hum. Gene Ther.*, 9(8):1233-1236, 1998.
Levinson et al., *Nature* 295:79, 1982.
Lin et al., *Mol. Cell. Biol.*, 10:850, 1990.
Luria et al., *EMBO J.*, 6:3307, 1987.
Lusky and Botchan, *Proc. Natl. Acad. Sci. USA*, 83:3609, 1986.
Lusky et al.,*Mol. Cell. Biol.*, 3:1108, 1983.
Macejak and Sarnow, *Nature* 353:90-94, 1991.
Majors and Varmus, *Proc. Natl. Acad. Sci. USA*, 80:5866, 1983.
Marketon et al., *Science*, 309:1739-1741, 2005.
McNeall et al., *Gene*, 76:81, 1989.
Merrifield, *Science*, 232(4748):341-347, 1986.
Meyer et al., *J Infect. Dis.*, 129:S30-S36, 1974.
Meyer, *Bacteriol. Rev.*, 25:249-261, 1961.
Meyer, *Bull. W.H.O.* 42:653-666, 1970.
Miksicek et al., *Cell*, 46:203, 1986.
Mordacq and Linzer, *Genes and Dev.*, 3:760, 1989.
Moreau et al., *Nucl. Acids Res.*, 9:6047, 1981.
Motin et al., *Infect. Immun.*, 62:4192-4201, 1994.
Motin et al., *Infect. Immun.*, 64:4313-4318, 1996.
Muesing et al., *Cell*, 48:691, 1987.
Nakajima et al., *Infect. Immun.*, 63:3021-3029, 1993.
Nakajima et al., *Infect. Immun.*, 63:3021-3029, 1995.
Ng et al., *Nuc. Acids Res.*, 17:601, 1989.
Nicolau and Sene, *Biochim, Biophys. Acta*, 721:185-190, 1982.
Nicolau et al., *Methods Enzymol.*, 149:157-176, 1987.
Nilles, *Structure*, 12:357-358, 2004.
Omirulleh et al., *Plant Mol. Biol.*, 21(3):415-28, 1993.
Ondek et al., *EMBO J.*, 6:1017, 1987.
Omitz et al., *Mol. Cell. Biol.*, 7:3466, 1987.
Overheim et al., *Infect. Immun.*, 73:5152-5159, 2005.
Palmiter et al., *Nature* 300:611, 1982.
PCT Appln. 95/06128
PCT Appln. PCT/US89/01025
PCT Appln. WO 94/09699
Pech et al., *Mol. Cell. Biol.*, 9:396, 1989.
Pelletier and Sonenberg, *Nature* 334(6180):320-325, 1988.
Perez-Stable and Constantini, *Mol. Cell. Biol.*, 10:1116, 1990.
Perry and Fetherston, *Clin. Microbiol. Rev.*, 10:35-66
Picard and Schaffner, *Nature* 307:83, 1984.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10: 1076, 1990.
Potrykus et al., *Mol. Gen. Genet.*, 199:183-188, 1985.
Pullen et al., *Infect. Immun.*, 66:521-527, 1998.
Queen and Baltimore, *Cell*, 35:741, 1983.
Quinn et al., *Mol. Cell. Biol.*, 9:4713, 1989.
Redondo et al., *Science*, 247:1225, 1990.

Reed and Muench, *Am. J. Hygiene,* 27:493-497, 1938.
Reisman and Rotter, *Mol. Cell. Biol.,* 9:3571, 1989.
Remington's Pharmaceutical Sciences 15th Edition, 33:624-652, 1990
Resendez Jr. et al., *Mol. Cell. Biol.,* 8:4579, 1988.
Ripe et al., *Mol. Cell. Biol.,* 9:2224, 1989.
Rippe et al., *Mol. Cell Biol.,* 10:689-695, 1990.
Rittling et al., *Nuc. Acids Res.,* 17:1619, 1989.
Rosen et al., *Cell,* 41:813, 1988.
Russel et al., *Vaccine,* 13:1551-1556, 1995.
Sakai et al., *Genes and Dev.,* 2:1144, 1988.
Sambrook et al., *In: Molecular cloning,* Cold Spring Harbor Laboratory Press, Cold Spring Harbor, NY, 2001.
Satake et al., *J. Virology,* 62:970, 1988.
Sawa et al., *Nat. Med.,* 5:392-398, 1999.
Schaffner et al., *J. Mol. Biol.,* 201:81, 1988.
Searle et al., *Mol. Cell. Biol.,* 5:1480, 1985.
Sharp and Marciniak, *Cell,* 59:229, 1989.
Shaul and Ben-Levy, *EMBO J.,* 6:1913, 1987.
Sherman et al., *Mol. Cell. Biol.,* 9:50, 1989.
Sing et al., *Int. J. Med. Microbiol.,* 293:341-348, 2003.
Sing et al., *J. Exp. Med.,* 196:1017-1024, 2002b.
Sing et al., *J. Immunol.,* 168:1315-1321, 2002a.
Skrzypek and Straley, *J. Bacteriol.,* 177:2530-2542, 1995.
Sleigh and Lockett, *J. EMBO,* 4:3831, 1985.
Spalholz et al., *Cell,* 42:183, 1985.
Spandau and Lee, *J. Virology,* 62:427, 1988.
Spandidos and Wilkie, *EMBO J.,* 2:1193, 1983.
Stephens and Hentschel, *Biochem. J.,* 248:1, 1987.
Stewart and Young, *In: Solid Phase Peptide Synthesis,* 2d. ed., Pierce Chemical Co., 1984.
Stuart et al., *Nature* 317:828, 1985.
Studier et al., *Methods Enzymol.,* 185:60-89, 1990.
Sullivan and Peterlin, *Mol. Cell. Biol.,* 7:3315, 1987.
Surgalla and Beesley, *Appl. Microbiol.,* 18:834-837, 1969.
Swartzendruber and Lehman, *J. Cell. Physiology,* 85:179, 1975.
Takebe et al., *Mol. Cell. Biol.,* 8:466, 1988.
Tam et al., *J. Am. Chem. Soc.,* 105:6442, 1983.
Tavernier et al., *Nature* 301:634, 1983.
Taylor and Kingston, *Mol. Cell. Biol.,* 10:165, 1990a.
Taylor and Kingston, *Mol. Cell. Biol.,* 10:176, 1990b.
Taylor et al., *J. Biol. Chem.,* 264:15160, 1989.
Thiesen et al., *J. Virology,* 62:614, 1988.
Thomson et al., *J. Immunol.,* 157(2):822-826, 1996.
Titball and Williamson, *Expert Opin. Biol. Ther.,* 4:965-973, 2004.
Treisman, *Cell,* 42:889, 1985.
Tronche et al., *Mol. Biol. Med.,* 7:173, 1990.
Trudel and Constantini, *Genes and Dev.,* 6:954, 1987.
Tyndell et al., *Nuc. Acids. Res.,* 9:6231, 1981.
Une and Brubaker, *J. Immunol.,* 133:2226-2230, 1984.
Vannice and Levinson, *J. Virology,* 62:1305, 1988.
Vasseur et al., *Proc. Natl. Acad. Sci. USA,* 77:1068, 1980.
Wake et al., *Immunology,* 34:1045-1052, 1978.
Wang and Calame, *Cell,* 47:241, 1986.
Wang et al., *Vaccine,* 22:3348-3357, 2004.
Weber et al., *Cell,* 36:983, 1984.
Weinberger et al., *Mol. Cell. Biol.,* 8:988, 1984.
Weinberger et al., *Science,* 228:740-742, 1985.
Welkos et al., *Vaccine,* 20:2206-2214, 2002.
Williams and Cavanaugh, *Bull. World Health Org.,* 57:309-313, 1979.
Winoto and Baltimore, *Cell,* 59:649, 1989.
Wolf et al., *Comput. Appl. Biosci.,* 4(1):187-191, 1988.
Wong et al., *Gene,* 10:87-94, 1980.
Yutzey et al. *Mol. Cell. Biol.,* 9:1397, 1989.
Ziegler, In: *The black death,* Alan Sutton Publishing Inc., Wolfeboro Falls, N.H., 1991.

---

What is claimed is:

1. An isolated *Yersinia* LcrV polypeptide comprising an internal deletion, wherein the deletion comprises amino acids 271-300 based on a *Y. pestis* LcrV polypeptide sequence.

2. The polypeptide of claim 1, wherein the *Yersinia* LcrV protein is from *Yersinia pestis*.

3. The polypeptide of claim 1, wherein the deletion is of up to 163 contiguous residues.

4. The polypeptide of claim 1, wherein the internal deletion is of up to 90 contiguous residues.

5. The polypeptide of claim 4, wherein the internal deletion extends into the region spanning amino acids 240 to 325.

6. The polypeptide of claim 1, wherein the LcrV protein is at least 275 residues in length.

7. The polypeptide of claim 1, wherein the polypeptide is comprised in a pharmacologically acceptable formulation.

8. The polypeptide of claim 1, wherein the polypeptide is conjugated to an adjuvant.

9. A polynucleotide encoding the polypeptide of claim 1.

10. The polynucleotide of claim 9, wherein the polynucleotide is a vector that comprises a nucleic acid sequence encoding the polypeptide.

11. A polynucleotide encoding the polypeptide of claim 2.

12. The polynucleotide of claim 11, wherein the polynucleotide is a vector that comprises a nucleic acid sequence encoding the polypeptide.

13. A method of stimulating an immune response against a *Yersinia* pathogen in a subject comprising administering to the subject an effective amount of a composition comprising the polypeptide of claim 1, wherein the composition is in a pharmacologically acceptable formulation.

14. The method of claim 13, wherein the polypeptide is administered to a subject infected with a *Yersinia* pathogen or suspect of being infected with a *Yersinia* pathogen.

15. The method of claim 13, wherein the composition is administered to the subject intranasally, intramuscularly, subcutaneously, orally, locally, by inhalation, or by injection.

16. A method for preparing the polypeptide of claim 1 comprising,
    (a) purifying the polypeptide from a host cell having a nucleic acid encoding the polypeptide.

17. The method of claim 16, further comprising formulating the isolated polypeptide in a pharmaceutically acceptable composition.

18. The method of claim 17, wherein the pharmaceutically acceptable composition further comprises an adjuvant.

19. A pharmaceutically acceptable composition comprising a purified LcrV polypeptide comprising an internal deletion in the region spanning amino acids 271-300 based on a *Y. pestis* LcrV polypeptide sequence.

20. The composition of claim 19, wherein the purified polypeptide comprises an internal deletion of amino acids 271-300 based on a *Y. pestis* LcrV polypeptide sequence.

21. A method for preparing the polypeptide of claim 19 comprising,
    (a) isolating the polypeptide from a host cell having a nucleic acid encoding the polypeptide.

22. The polypeptide of claim 2, wherein the deletion consists essentially of amino acids 271-300.

23. An isolated Yersinia LcrV polypeptide comprising an internal deletion consisting of amino acids 181-210 based on a *Y. pestis* LcrV polypeptide sequence, wherein the polypeptide has a deletion of at most 30 amino acids.

24. The polypeptide of claim 23, wherein the *Yersinia* LcrV protein is from *Yersinia pestis*.

25. The polypeptide of claim 23, wherein the polypeptide is comprised in a pharmacologically acceptable formulation.

26. The polypeptide of claim 23, wherein the polypeptide is conjugated to an adjuvant.

27. An isolated *Yersinia* LcrV polypeptide comprising an internal deletion, wherein the internal deletion is of at least amino acids 181-210 based on a *Y. pestis* LcrV polypeptide sequence and the deletion is up to 163 contiguous residues.

28. The polypeptide of claim 27, wherein the internal deletion is of up to 90 contiguous residues.

29. The polypeptide of claim 27, wherein the internal deletion extends into the region spanning amino acids 240 to 325.

30. The polypeptide of claim 27, wherein the LcrV protein is at least 275 residues in length.

31. The polypeptide of claim 27, wherein the polypeptide is comprised in a pharmacologically acceptable formulation.

32. The polypeptide of claim 27, wherein the polypeptide is conjugated to an adjuvant.

* * * * *

UNITED STATES PATENT AND TRADEMARK OFFICE
CERTIFICATE OF CORRECTION

PATENT NO. : 7,875,280 B2  
APPLICATION NO. : 11/293024  
DATED : January 25, 2011  
INVENTOR(S) : Olaf Schneewind et al.

It is certified that error appears in the above-identified patent and that said Letters Patent is hereby corrected as shown below:

In title page, item (75) Inventors, delete "Colombus" and insert --Columbus-- as city of residence of Inventor Robert Brubaker.

In column 1, lines 7-9, delete
"The government may own rights in the present invention pursuant to grant number 1-U54-A1-057153 from the National Institutes of Health." and insert
--This invention was made with government support under grant number 1-U54-A1-057153 awarded by the National Institutes of Health. The government has certain rights in the invention--.

Signed and Sealed this
Third Day of May, 2011

David J. Kappos
*Director of the United States Patent and Trademark Office*

SEQUENCE LISTING

<160> NUMBER OF SEQ ID NOS: 44

<210> SEQ ID NO 1
<211> LENGTH: 325
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 1

Met Ile Arg Ala Tyr Glu Gln Asn Pro Gln His Phe Ile Glu Asp Leu
 1               5                  10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln

```
                100                 105                 110
Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
    130                 135                 140

His His Gly Asp Ala Arg Lys Leu Arg Glu Glu Leu Ala Glu Leu Thr
145                 150                 155                 160

Ala Glu Leu Lys Ile Tyr Ser Val Ile Gln Ala Glu Ile Asn Lys His
                165                 170                 175

Leu Ser Ser Ser Gly Thr Ile Asn Ile His Asp Lys Ser Ile Asn Leu
            180                 185                 190

Met Asp Lys Asn Leu Tyr Gly Tyr Thr Asp Glu Glu Ile Phe Lys Ala
        195                 200                 205

Ser Ala Glu Tyr Lys Ile Leu Glu Lys Met Pro Gln Thr Thr Ile Gln
    210                 215                 220

Val Asp Gly Ser Glu Lys Lys Ile Val Ser Ile Lys Asp Phe Leu Gly
225                 230                 235                 240

Ser Glu Asn Lys Arg Thr Gly Ala Leu Gly Asn Leu Lys Asn Ser Tyr
                245                 250                 255

Ser Tyr Asn Lys Asp Asn Glu Leu Ser His Phe Ala Thr Thr Cys
            260                 265                 270

Ser Asp Lys Ser Arg Pro Leu Asn Asp Leu Val Ser Gln Lys Thr Thr
        275                 280                 285

Gln Leu Ser Asp Ile Thr Ser Arg Phe Asn Ser Ala Ile Glu Ala Leu
    290                 295                 300

Asn Arg Phe Ile Gln Lys Tyr Asp Ser Val Met Gln Arg Leu Leu Asp
305                 310                 315                 320

Asp Thr Ser Gly Lys
                325

<210> SEQ ID NO 2
<211> LENGTH: 326
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 2

Met Ile Arg Ala Tyr Glu Gln Asn Pro Gln His Phe Ile Glu Asp Leu
1               5                   10                  15

Glu Asn Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Arg Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125
```

```
Asp Arg Ile Asp Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
                180                 185                 190

Leu Met Asp Lys Asn Leu Tyr Gly Tyr Thr Asp Glu Ile Phe Lys
                195                 200                 205

Ala Ser Ala Glu Tyr Lys Ile Leu Glu Lys Met Pro Gln Thr Thr Ile
210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
                260                 265                 270

Ser Ser Asp Lys Ser Arg Pro Leu Asn Asp Leu Val Ser Gln Lys Thr
                275                 280                 285

Thr Gln Leu Ser Asp Ile Thr Ser Arg Phe Asn Ser Ala Ile Glu Ala
290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 3
<211> LENGTH: 326
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 3

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
                20                  25                  30

Glu Glu Leu Val Gln Leu Val Lys Asp Lys Asn Ile Asp Ile Ser Ile
            35                  40                  45

Lys Tyr Asp Pro Arg Lys Asp Ser Glu Val Phe Ala Asn Arg Val Ile
        50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160
```

```
Thr Ala Glu Leu Lys Ile Tyr Ser Val Ile Gln Ala Glu Ile Asn Lys
            165                 170                 175

His Leu Ser Ser Ser Gly Thr Ile Asn Ile His Asp Lys Ser Ile Asn
        180                 185                 190

Leu Met Asp Lys Asn Leu Tyr Gly Tyr Thr Asp Glu Glu Ile Phe Lys
    195                 200                 205

Ala Ser Ala Glu Tyr Lys Ile Leu Glu Lys Met Pro Gln Thr Thr Ile
210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 4
<211> LENGTH: 324
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 4

Met Ile Arg Ala Tyr Glu Gln Asn Pro Gln His Phe Ile Glu Asp Leu
 1               5                  10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
```

```
                       180                 185                 190
Leu Met Asp Lys Asn Leu Tyr Gly Tyr Thr Asp Glu Glu Ile Phe Lys
            195                 200                 205
Ala Ser Ala Glu Tyr Lys Ile Leu Glu Lys Met Pro Gln Thr Thr Ile
        210                 215                 220
Gln Val Asp Gly Ser Glu Lys Lys Ile Val Ser Ile Lys Asp Phe Leu
225                 230                 235                 240
Gly Ser Glu Asn Lys Arg Thr Gly Ala Leu Gly Asn Leu Lys Asn Ser
                245                 250                 255
Tyr Ser Tyr Asn Lys Asp Asn Glu Leu Ser His Phe Ala Thr Thr
            260                 265                 270
Cys Ser Asp Lys Ser Arg Pro Leu Asn Asp Leu Val Ser Gln Lys Thr
        275                 280                 285
Thr Gln Leu Ser Asp Ile Thr Ser Arg Phe Asn Ser Ala Ile Glu Ala
        290                 295                 300
Leu Asn Arg Phe Ile Gln Lys Tyr Asp Ser Val Met Gln Arg Leu Leu
305                 310                 315                 320

Asp Asp Thr Arg

<210> SEQ ID NO 5
<211> LENGTH: 326
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 5

Met Ile Arg Ala Tyr Glu Gln Asn Pro Gln His Phe Ile Glu Asp Leu
1               5                   10                  15
Glu Lys Val Arg Val Glu Gln Leu Thr Gly His Gly Ser Ser Val Leu
            20                  25                  30
Glu Glu Leu Val Gln Leu Val Lys Asp Lys Asn Ile Asp Ile Ser Ile
        35                  40                  45
Lys Tyr Asp Pro Arg Lys Asp Ser Glu Val Phe Ala Asn Arg Val Ile
    50                  55                  60
Thr Asp Asp Ile Glu Leu Leu Lys Lys Ile Leu Ala Tyr Phe Leu Pro
65                  70                  75                  80
Glu Asp Ala Ile Leu Lys Gly Gly His Tyr Asp Asn Gln Leu Gln Asn
                85                  90                  95
Gly Ile Lys Arg Val Lys Glu Phe Leu Glu Ser Ser Pro Asn Thr Gln
            100                 105                 110
Trp Glu Leu Arg Ala Phe Met Ala Val Ile His Phe Ser Leu Thr Ala
        115                 120                 125
Asp Arg Ile Asp Asp Ile Leu Lys Val Ile Val Asp Ser Met Asn
        130                 135                 140
His His Gly Asp Ala Arg Ser Lys Leu Arg Glu Glu Leu Ala Glu Leu
145                 150                 155                 160
Thr Ala Glu Leu Lys Ile Tyr Ser Val Ile Gln Ala Glu Ile Asn Lys
                165                 170                 175
His Leu Ser Ser Gly Thr Ile Asn Ile His Asp Lys Ser Ile Asn
            180                 185                 190
Leu Met Asp Lys Asn Leu Tyr Gly Tyr Thr Asp Glu Glu Ile Phe Lys
        195                 200                 205
Ala Ser Ala Glu Tyr Lys Ile Leu Glu Lys Met Pro Gln Thr Thr Ile
    210                 215                 220
```

```
                210                 215                 220
Gln Glu Gly Glu Thr Glu Lys Lys Ile Val Ser Ile Lys Asn Phe Leu
225                 230                 235                 240

Glu Ser Glu Lys Lys Arg Thr Gly Ala Leu Gly Asn Leu Lys Asp Ser
                245                 250                 255

Tyr Ser Tyr Asn Lys Asp Asn Asn Glu Leu Ser His Phe Ala Thr Thr
                260                 265                 270

Cys Ser Asp Lys Ser Arg Pro Leu Asn Asp Leu Val Ser Gln Lys Thr
                275                 280                 285

Thr Gln Leu Ser Asp Ile Thr Ser Arg Phe Asn Ser Ala Ile Glu Ala
290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 6
<211> LENGTH: 333
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 6

Met Ile Arg Ala Tyr Glu Gln Asn Pro Gln His Phe Ile Glu Asp Leu
  1               5                  10                  15

Glu Lys Val Arg Val Glu Gln Leu Thr Gly His Gly Ser Ser Val Leu
                 20                  25                  30

Glu Glu Leu Val Gln Leu Val Lys Asp Lys Ile Asp Ile Ser Ile
             35                  40                  45

Lys Tyr Asp Pro Lys Lys Asp Ser Glu Val Phe Ala Glu Arg Val Ile
 50                  55                  60

Thr Asp Asp Ile Glu Leu Leu Lys Lys Ile Leu Ala Tyr Phe Leu Pro
 65                  70                  75                  80

Glu Asp Ala Ile Leu Lys Gly Gly His Tyr Asp Asn Gln Leu Gln Asn
                 85                  90                  95

Gly Ile Lys Arg Val Lys Glu Phe Leu Glu Ser Ser Pro Asn Thr Gln
                100                 105                 110

Trp Glu Leu Arg Ala Phe Met Ala Val Met His Phe Ser Leu Thr Ala
            115                 120                 125

Asp Arg Ile Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Glu Lys Ser Ile Asn
                180                 185                 190

Leu Met Asp Lys Asn Leu Tyr Gly Tyr Thr Asp Glu Glu Ile Phe Lys
            195                 200                 205

Ala Ser Ala Glu Tyr Lys Ile Leu Lys Lys Met Pro Gln Thr Thr Ile
                210                 215                 220

Lys Asp Asp Glu Leu His Glu Val Gly Val Ile Ala Gly Ala Glu Lys
225                 230                 235                 240
```

```
Gln Ile Val Ser Ile Lys Asn Phe Leu Glu Ser Glu Asn Lys Arg Thr
                245                 250                 255
Gly Ala Leu Gly Asn Leu Lys Asp Ser Tyr Ser Tyr Asn Lys Asp Asn
            260                 265                 270
Asn Glu Leu Ser His Phe Ala Thr Ala Cys Ser Asp Lys Ser Arg Pro
        275                 280                 285
Leu Asn Asp Leu Val Ser Gln Lys Thr Thr Gln Leu Ser Asp Ile Thr
    290                 295                 300
Ser Arg Phe Asn Ser Ala Ile Glu Ala Leu Asn Arg Phe Ile Gln Lys
305                 310                 315                 320
Tyr Asp Ser Val Met Gln Arg Leu Leu Asp Asp Thr Arg
                325                 330

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 7

Val Leu Glu Glu Leu Val Gln Leu Val Lys Asp Lys Lys Ile Asp Ile
  1               5                  10                  15
Ser Ile Lys

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 8
aacatatggt tttagaagaa ttggttcagt t                               31

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 9
aaggatcctt taccagacgt gtcatc                                     26

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 10
aaggtaccaa tagagtaatt actgatgata tc                              32

<210> SEQ ID NO 11
<211> LENGTH: 26
<212> TYPE: DNA
<213> ORGANISM: Artificial Sequence
<220> FEATURE:
```

<223> OTHER INFORMATION: Description of Artificial Sequence:
      Synthetic Primer

<400> SEQUENCE: 11
aaggatcctt taccagacgt gtcatc                                            26

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 12
aacatatgat tagagcctac gaacaa                                            26

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 13
aaggtaccgg caaaaacctc cgaatcttt                                         29

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 14
aaggtaccga caaccaactg caaaatgg                                          28

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 15
aaggatcctt taccagacgt gtcatc                                            26

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 16
aacatatgat tagagcctac gaacaa                                            26

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:

Synthetic Primer

<400> SEQUENCE: 17
aaggtaccat aatgaccgcc tttaagaatg                                30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 18
aaggtaccgt aatgcatttc tctttaaccg                                30

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 19
aaggatcctt taccagacgt gtcatc                                    26

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 20
aacatatgat tagagcctac gaacaa                                    26

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 21
aaggtacctg ccatgaacgc ccgcaat                                   27

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 22
aaggtaccag caagttgcgt gaagaatta                                 29

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence:
      Synthetic Primer

```
<400> SEQUENCE: 23
aaggatcctt taccagacgt gtcatc                                          26

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 24
aacatatgat tagagcctac gaacaa                                          26

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 25
aaggtaccac gggcatcacc atgatgat                                        28

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 26
aaggtaccag tggcaccata aatatccat                                       29

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 27
aaggatcctt taccagacgt gtcatc                                          26

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 28
aacatatgat tagagcctac gaacaa                                          26

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer
```

<400> SEQUENCE: 29
aaggtaccac tagacagatg cttattaatt t                              31

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 30
aaggtaccgc agagtacaaa attctcgag                                 29

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 31 aaggatccttt taccagacgt gtcatc                                    26

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 32
aacatatgat tagagcctac gaacaa                                    26

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 33
aaggtaccgc tggctttaaa aatctcttca                                30

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 34
aaggtaccgg aagtgagaat aaaagaacc                                 29

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 35
aaggatcctt taccagacgt gtcatc                                    26

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 36
aacatatgat tagagcctac gaacaa                                    26

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 37
aaggtaccaa gaaagtcctt tatcgagact                                30

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 38
aaggtaccac cacctgctcg gataagt                                   27

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 39
aaggatcctt taccagacgt gtcatc                                    26

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 40
aacatatgat tagagcctac gaacaa                                    26

<210> SEQ ID NO 41
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 41

-continued

```
aaggtaccgg caaagtgaga taattcatta t                                        31
```

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 42

```
aacatatgat tagagcctac gaacaa                                              26
```

<210> SEQ ID NO 43
<211> LENGTH: 32
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 43

```
aaggatcctg aattaaaacg tgatgtaata tc                                       32
```

<210> SEQ ID NO 44
<211> LENGTH: 294
<212> TYPE: PRT
<213> ORGANISM: Pseudomonas aeruginosa

<400> SEQUENCE: 44

```
Met Glu Val Arg Asn Leu Asn Ala Ala Arg Glu Leu Phe Leu Asp Glu
  1               5                  10                  15

Leu Leu Ala Ala Ser Ala Ala Pro Ala Ser Ala Glu Gln Glu Glu Leu
             20                  25                  30

Leu Ala Leu Leu Arg Ser Glu Arg Ile Val Leu Ala His Ala Gly Gln
         35                  40                  45

Pro Leu Ser Glu Ala Gln Val Leu Lys Ala Leu Ala Trp Leu Leu Ala
     50                  55                  60

Ala Asn Pro Ser Ala Pro Pro Gly Gln Gly Leu Glu Val Leu Arg Glu
 65                  70                  75                  80

Val Leu Gln Ala Arg Arg Gln Pro Gly Ala Gln Trp Asp Leu Arg Glu
                 85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
        115                 120                 125

Lys Ala Leu Leu Asp Glu Leu Lys Ala Leu Thr Ala Glu Leu Lys Val
    130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
        195                 200                 205

Asp Phe Leu Ser Gly Ser Pro Lys Gln Ser Gly Glu Leu Lys Gly Leu
    210                 215                 220

Ser Asp Glu Tyr Pro Phe Glu Lys Asp Asn Asn Pro Val Gly Asn Phe
```

```
                 225                 230                 235                 240
Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
                260                 265                 270

Val Glu Ala Leu Asn Arg Phe Ile Gln Lys Tyr Asp Ser Val Leu Arg
            275                 280                 285

Asp Ile Leu Ser Ala Ile
            290
```